US010080784B2

(12) United States Patent
Parker et al.

(10) Patent No.: US 10,080,784 B2
(45) Date of Patent: Sep. 25, 2018

(54) ENHANCED THERAPEUTIC USAGE OF A PURINE NUCLEOSIDE PHOSPHORYLASE OR NUCLEOSIDE HYDROLASE PRODRUG

(75) Inventors: William B. Parker, Birmingham, AL (US); Eric J. Sorscher, Birmingham, AL (US)

(73) Assignees: SOUTHERN RESEARCH INSTITUTE, Birmingham, AL (US); THE UAB RESEARCH FOUNDATION, Birmingham, AL (US)

( * ) Notice: Subject to any disclaimer, the term of this patent is extended or adjusted under 35 U.S.C. 154(b) by 761 days.

(21) Appl. No.: 14/000,367

(22) PCT Filed: Feb. 20, 2012

(86) PCT No.: PCT/US2012/025816
§ 371 (c)(1),
(2), (4) Date: Aug. 19, 2013

(87) PCT Pub. No.: WO2012/112984
PCT Pub. Date: Aug. 23, 2012

(65) Prior Publication Data
US 2013/0330315 A1  Dec. 12, 2013

Related U.S. Application Data

(60) Provisional application No. 61/444,261, filed on Feb. 18, 2011.

(51) Int. Cl.
A61K 38/47 (2006.01)
A61K 38/45 (2006.01)
A61K 38/46 (2006.01)
A61K 31/7076 (2006.01)
A61K 48/00 (2006.01)
A61K 9/06 (2006.01)
A61K 9/16 (2006.01)

(52) U.S. Cl.
CPC ......... *A61K 38/47* (2013.01); *A61K 9/06* (2013.01); *A61K 9/1641* (2013.01); *A61K 9/1647* (2013.01); *A61K 31/7076* (2013.01); *A61K 38/45* (2013.01); *A61K 38/465* (2013.01); *A61K 48/00* (2013.01); *Y02A 50/473* (2018.01)

(58) Field of Classification Search
None
See application file for complete search history.

(56) References Cited

U.S. PATENT DOCUMENTS

| 5,081,110 A * | 1/1992 | Kim ............... A61K 31/70 514/47 |
| 2004/0067953 A1* | 4/2004 | Stein ............... A61K 31/337 514/251 |
| 2005/0186179 A1* | 8/2005 | Harats ............... A61K 48/0058 424/93.2 |
| 2006/0177423 A1* | 8/2006 | Both ............... A61K 38/45 424/93.2 |
| 2009/0123546 A1 | 5/2009 | Ashton et al. |
| 2011/0212073 A1* | 9/2011 | Parker ............... A61K 38/45 424/94.5 |

FOREIGN PATENT DOCUMENTS

| WO | 2003035012 A2 | 5/2003 |
| WO | 2010019954 A2 | 2/2010 |

OTHER PUBLICATIONS

Parker WB, Allan PW, Shaddix SC, Rose LM, Speegle HF, Gillespie GY, and Bennett LL Jr. Metabolism and metabolic actions of 6-methylpurine and 2-fluoroadenine in human cells. Biochem. Pharmacol. 1998; 55: 1673-1681.

Martiniello-Wilks R, Garcia-Aragon J, Daja MM, Russell P, Both GW, Molloy PL, Lockett LJ, and Russell PJ. In vivo gene therapy for prostate cancer: Preclinical evaluation of two different enzyme-directed prodrug therapy systems delivered by identical adenovirus vectors. Human Gene Therapy 1998; 9: 1617-1626.

Mohr L, Shankara S, Yoon SK, Krohne TU, Geissler M, Roberts B, Blum HE, and Wands JR. Gene therapy of hepatocellular carcinoma in vitro and in vivo in nude mice by adenoviral transfer of the *Escherichia coli* purine nucleoside phosphorylase gene. Hepatology 2000; 31: 606-614.

Parker WB, Allan PW, Hassan AEA, Secrist JA III, Sorscher EJ, and Waud WR. Antitumor activity of 2-fluoro-2'-deoxyadenosine against tumors that express *Escherichia coli* purine nucleoside phosphorylase. Cancer Gene Therapy 2003; 10: 23-29.

Parker WB, King SA, Allan PW, Bennett LL Jr, Secrist JA III, Montgomery JA, Gilbert KS, Waud WR, Wells AH, Gillespie GY, and Sorscher EJ. In vivo gene therapy of cancer with *E. coli* purine nucleoside phosphorylase. Human Gene Therapy 1997; 8: 1637-1644.

Deharvengt S, Rejiba S, Wack S, Aprahamian M, Hajri A. Efficient electrogene therapy for pancreatic adenocarcinoma treatment using the bacterial purine nucleoside phosphorylase suicide gene with fludarabine. Int. J. Oncol. 2007; 30: 1397-1406.

(Continued)

*Primary Examiner* — Christopher M Babic
*Assistant Examiner* — Kimberly A Aron
(74) *Attorney, Agent, or Firm* — Avery N. Goldstein; Blue Filament Law, PLLC

(57) ABSTRACT

The use of a purine nucleoside phosphorylase or nucleoside hydrolase or a vector encoding expression of one of these enzymes is detailed along with the use of a prodrug cleaved by the purine nucleoside phosphorylase or nucleoside hydrolase for the preparation of a direct injection inhibition of replicating or non-replicating targeted cells. The targeted cells do not normally express the introduced purine nucleoside phosphorylase or nucleoside hydrolase. The enzyme and prodrug are amenable to intermixing and injection as a single dose or as separate injection or administration to the targeted cells. The substance and prodrug efficacy are enhanced through exposure of the targeted cells to X-ray radiation. Administration of a prodrug regardless of administration route to the targeted cells is effective in combination with X-ray radiation therapy to kill or inhibit function of the targeted cells.

15 Claims, 16 Drawing Sheets

(56) References Cited

OTHER PUBLICATIONS

Kikuchi E, Menendez S, Ozu C, Ohori M, Cordon-Cardo C, Logg CR, Kasahara N, Bochner BH. Delivery of replication-competent retrovirus expressing *Escherichia coli* purine nucleoside phosphorylase increases the metabolism of the prodrug, fludarabine phosphate and suppresses the growth of bladder tumor xenografts. Cancer Gene Ther. 2007; 14: 279-86.

Lockett LJ, Molloy PL, Russell PJ, Both GW. Relative efficiency of tumor cell killing in vitro by two enzyme-prodrug systems delivered by identical adenovirus vectors. Clin Cancer Res 1997; 3:2075-80.

Nestler U, Heinkelein M, Lucke M, Meixensberger J, Scheurlen W, Kretschmer A, Rethwilm A. Foamy virus vectors for suicide gene therapy. Gene Therapy 1997; 4:1270-77.

Puhlmann M, Gnant M, Brown CK, Alexander HR, and Bartlett DL. Thymidine kinase-deleted vaccinia virus expressing purine nucleoside phosphorylase as a vector for tumor-directed gene therapy. Human Gene Therapy 1999; 10: 649-657.

Gadi VK, Alexander SD, Waud WR, Allan PW, Parker WB, and Sorscher EJ. A long-acting suicide gene toxin, 6-methylpurine, inhibits slow growing tumors after a single administration. J. Pharmacol. Exp. Ther. 2003; 304: 1280-1284.

Hong JS, Waud WR, Levasseur DN, Townes TM, Wen H, McPherson SA, Moore BA, Bebok Z, Allan PW, Secrist JA 3rd, Parker WB, and Sorscher EJ. Excellent In vivo Bystander Activity of Fludarabine Phosphate against Human Glioma Xenografts that Express the *Escherichia coli* Purine Nucleoside Phosphorylase Gene. Cancer Res. 2004; 64: 6610-6615.

Fu W, Lan H, Li S, Han X, Gao T, Ren D. Synergistic antitumor efficacy of suicide/ePNP gene and 6-methylpurine 2'-deoxyriboside via Salmonella against murine tumors.

Fu W, Lan H, Liang S, Gao T, Ren D. Suicide gene/prodrug therapy using salmonella-mediated delivery of *Escherichia coli* purine nucleoside phosphorylase gene and 6 methoxypurine 2-deoxyriboside in murine mammary carcinoma 4T1 model. Cancer Sci. 2008; 99: 1172-1179.

Parker WB, Allan PW, Waud WR, Hong JS, Sorscher EJ (2010) Effect of expression of adenine phosphoribosyltransferase on the in vivo anti-tumor activity of prodrugs activated by *E. coli* purine nucleoside phosphorylase. Cancer Gene Therapy in press.

Voeks, D. et al., Gene Therapy for Prostate Cancer Delivered by Ovine Adenovirus and Mediated by Purine Nucleoside Phosphorylase and Fludarabine in Mouse Models, Gene Therapy, Jun. 2002, vol. 9, No. 12, pp. 759-768.

Martiniello-Wilks, R. et al., Purine Nucleoside Phosphorylase and Fludarabine Phosphate Gene-Directed Enzyme Prodrug Therapy Suppresses Primary Tumour Growth and Pseudo-Metastases in a Mouse Model of Prostate Cancer, The Journal of Gene Medicine, Dec. 2004, vol. 6, No. 12, pp. 1343-1357.

Martiniello-Wilks, R. et al., Gene-Directed Enzyme Prodrug Therapy for Prostate Cancer in a Mouse Model That Imitates the Development of Human Disease, The Journal of Gene Medicine, Jan. 2004, vol. 6, No. 1, pp. 43-54.

Nitsche, M. et al., The Combined Effect of Fludarabine Monophosphate and Radiation as well as Gemcitabine and Radiation on Squamous Carcinoma Tumor Cell Lines in Vitro, Int. J. Radiat. Biol., Aug. 2008, vol. 84, No. 8, pp. 643-657.

Sang L, Roberts JM, Coller HA. Hijacking HES1: How tumors co-opt the anti-differentiation strategies of quiescent cells. Trends Mol Med 2010; 16(1):17-26.

Mellor HR, Ferguson DJP, Callaghan R. A model of quiescent tumor microregions for evaluating multicellular resistance to chemotherapeutic drugs. Br J Cancer 2005; 93(3):302-9.

Vessella RL, Pantel K, Mohla S. Tumor cell dormancy: an NCI workshop report. Cancer Biol Ther 2007; 6(9):1496-504.

Kusumbe AP, Bapat SA. Cancer stem cells and aneuploid populations within developing tumors are the major determinants of tumor dormancy. Cancer Res 2009; 69(24):9245-53.

Osada S, Yoshida K, Saji S. A novel strategy by cryoablation for advanced hepatoma. Anticancer Res 2009; 29(12):5203-9.

Krishnan S, Diagaradjane P, Cho SH. Nanoparticle-mediated thermal therapy: Evolving strategies for prostate cancer therapy. Int J Hyperthermia Sep. 21, 2010 [Epub ahead of print].

Margreiter M, Marberger M. Focal therapy and imaging in prostate and kidney cancer: High-intensity focused ultrasound ablation of small renal tumors. J Endourol 2010; 24(5): 745-6.

Both GW. Recent progress in gene-directed enzyme prodrug therapy: an emerging cancer treatment. Curr Opin Mol Ther 2009; 11(4): 421-32. (Abstract only).

Altaner C. Prodrug gene therapy. Cancer Lett 2008; 270(2): 191-201.

Dachs GU, Hunt MA, Syddall S, Singleton DC, Patterson AV. Bystander or no bystander for gene directed enzyme prodrug therapy. Molecules 2009; 14(11): 4517-45.

Ungerechts G, Springfield C., Frenzke ME, Lampe J, Johnston P, Parker WB, Sorscher EJ, Cattaneo R. Lymphoma chemovirotherapy: CD20-targeted and convertase-armed measles virus can synergize with fludarabine. Cancer Res. 2007; 67: 10939-10947.

Takimoto, Chris, MD, PhD and Calvo, Emiliano MD, PhD "Principles of Oncologic Pharmacotherapy", Published on Physicians Practice (http://www.physicianspractice.com), pp. 1-16; Jan. 1, 2005.

Sharma, Ricky A., et al. Clinical Development of New Drug-Radiotherapy Combinations, Nature Reviews/Clinical Oncology; Advance Online Publication, www.nature.com/nrclinonc; pp. 16; © Jun. 1, 2016 Macmillan Publishers Limited. All rights reserved.

Glynne-Jones, Rob et al. "Drug Combinations in Preoperative Chemoradiation for Rectal Cancer", http://dx.doi.org/10.1016/j.semradonc.2016.02.002; 1053-4296// © 2016 Elsevier Inc. pp. 211-219.

Wilson, George D., et al. "Biologic Basis for Combining Drugs With Radiation", 1053-4296/06/$—see front matter © 2006 Elsevier Inc.; pp. 1-8; All rights reserved.

Combs, Stephanie E., et al. In Vitro Responsiveness of Glioma Cell Lines to Multimodality Treatment With Radiotherapy, Temozolomide, and Epidermal Growth Factor Receptor Inhibition With Cetuximab; I. J. Radiation Oncology, Biology, Physics vol. 68, No. 3, pp. 873-874; Elsevier.

* cited by examiner

● saline
○ 3 mg F-araAMP injected into tumor (q1dx3, day 13) ------ 120 mg/kg
▼ 3 mg F-araAMP injected into tumor (q1dx3, q6hx2, day 13)

ENHANCED THERAPEUTIC USAGE OF A PURINE NUCLEOSIDE PHOSPHORYLASE OR NUCLEOSIDE HYDROLASE PRODRUG

RELATED APPLICATIONS

This application claims priority benefit of U.S. Provisional Application Ser. No. 61/444,261, filed 18 Feb. 2011, the contents of which are hereby incorporated by reference.

GOVERNMENT LICENSE RIGHTS

This invention was made with government support under CA119170 awarded by the National Institutes of Health. The government has certain rights in the invention.

FIELD OF THE INVENTION

The present invention relates in general to inducing cell death through controlled situ in vivo cleavage of a prodrug to yield a cytotoxic and in particular to enhancement therapeutic effect by practicing cleavage in concert with direct in situ injection of the prodrug, therapeutic radiation, or a combination thereof.

BACKGROUND OF THE INVENTION

Chemotherapy is a mainstay for treatment of many human tumors, but in vivo efficacy against quiescent or slowly dividing cancers is poor (Takimoto et al. *Cancer Management Handbook* (11th Edition), UBM Medica 2009; Sang et al. *Trends Mol Med* 2010; 16(1):17-26; Mellor et al. *Br J Cancer* 2005; 93(3):302-9). Radiotherapy and systemically administered chemotherapy achieve specificity by disrupting DNA replication, but cannot ablate quiescent tumor tissues that cycle intermittently. The inability to destroy nondividing tumor cells (including a putative tumor stem cell compartment) is acknowledged as one reason for failure against common human malignancies, including low-growth fraction tumors of prostate, breast, lung, and colon, among many others (Vessella et al. *Cancer Biol Ther* 2007; 6(9):1496-504; Kusumbe et al. *Cancer Res* 2009; 69(24): 9245-53). Even in the case of a solid tumor with an uncharacteristically high mitotic index (e.g. growth fraction ~40%), and assuming that all dividing cancer cells are completely destroyed by a cumulative exposure to conventional chemo- or radiotherapy, the mass would still be less than one doubling away from achieving pretreatment dimensions.

Non-metastatic cancers of breast, prostate, larynx, and brain are commonly treated with preoperative radiation therapy (XRT) as a debulking measure prior to definitive surgical resection (DeVita et al. *Principles and Practice of Oncology* (8th Edition). Ronald A. DePinho and Robert A. Weinbert, Eds. Lippincott Williams & Wilkins, 2008). Other locally invasive, non-metastatic tumors are suitable for life-prolonging XRT, and inoperable malignancies that obstruct a viscus (e.g., stomach, larynx, colon, or airway) are routinely treated with local radiotherapy for palliation (Washington et al. *Principles and Practice of Radiation Therapy* (3rd Edition). Mosby, 2009). Tumors such as these invariably exhibit a low growth fraction, and at some point become unresponsive to both radio- and the best available chemotherapies.

Several newer modalities have been advanced in an attempt to improve treatment of locally invasive, non-metastatic tumors, including common cancers such as those described above. Cryogenic, magnetic, thermal, and ultrasonic cell ablative technologies, for example, have all been investigated with varying degrees of preclinical or early clinical success (Osada et al. *Anticancer Res* 2009; 29(12): 5203-9; Krishnan et al. *Int J Hyperthermia* 2010 Sep. 21 [Epub ahead of print]; Margreiter et al. *J Endourol* 2010; 24(5): 745-6). Experimental gene therapies, such as GDEPT (gene directed enzyme prodrug therapy; so-called "suicide gene" strategies), have been extensively tested, but have met with limited success against locally invasive, non-metastatic tumors for at least two reasons (G W Both. *Curr Opin Mol Ther* 2009; 11(4): 421-32; Altaner et al. *Cancer Lett* 2008; 270(2): 191-201; Dachs et al. *Molecules* 2009; 14(11): 4517-45). First, the efficiency of tumor cell transduction is low with currently available gene transfer vectors. The small proportion of malignant cells that express an anticancer transgene is often not adequate to mount a robust bystander effect against untransduced cells in the tumor mass. Second, GDEPT has primarily utilized the herpes simplex virus thymidine kinase (HSV-tk) gene or prokaryotic cytosine deaminase (CD) gene to activate intratumoral chemotherapy, and the compounds produced by these two enzymes (gancyclovir monophosphate and 5-fluorouracil (FUra), respectively) are primarily active against dividing tumor cells. Low transduction efficiency, poor bystander activity, and failure to kill nondividing cancer cells account for the failure of first generation GDEPT approaches against non-metastatic, solid tumors in the clinic.

The *E. coli* purine nucleoside phosphorylase (PNP) gene has been shown to generate highly potent compounds such as 2-fluoroadenine (F-Ade) or 6-methylpurine (MeP) intratumorally (Ungerechts et al. *Cancer Res*. 2007; 67: 10939-10947; Fu et al. *Cancer Gene Ther*. 2008; 15: 474-484; Fu W, Lan et al. *Cancer Sci*. 2008; 99: 1172-1179; Parker et al. *Cancer Gene Therapy* 2011 June; 18(6):390-8; Gadi et al. *J. Pharmacol. Exp. Ther.* 2003; 304: 1280-1284). Purine bases such as these diffuse freely between *E. coli* PNP transduced and neighboring (bystander) cells via facilitated diffusion pathways ubiquitous in all cells, and confer a pronounced bystander killing effect (Hong et al. *Cancer Res*. 2004; 64: 6610-6615). The compounds act by a unique mechanism that disrupts RNA and protein synthesis, and are therefore active against both dividing and nondividing (quiescent) tumor cells in vivo (Parker et al. *Biochem. Pharmacol*. 1998; 55: 1673-1681). F-Ade can be generated by intracellular *E. coli* PNP from prodrugs such as 2-F-2'-deoxyadenosine (F-dAdo) or fludarabine phosphate (F-araAMP) (Hong et al. *Cancer Res*. 2004; 64: 6610-6615; Parker et al. *Biochem. Pharmacol*. 1998; 55: 1673-1681; Martiniello-Wilks et al. *Human Gene Therapy* 1998; 9: 1617-1626; Mohr et al. *Hepatology* 2000; 31: 606-614; Voeks et al. *Gene Therapy* 2002; 9: 759-768; Martiniello-Wilks et al. *J. Gene Med.* 2004; 6: 1343-1357; Parker et al. *Cancer Gene Therapy* 2003; 10: 23-29; Parker et al. *Human Gene Therapy* 1997; 8: 1637-1644; Martiniello-Wilks et al. *J. Gene Med.* 2004; 6: 43-54). The latter agent, F-araAMP, is clinically approved for treatment of chronic lymphocytic leukemia, but has no activity against non-lymphoid malignancies.

F-Ade is approximately 1,000 times more active as an anticancer agent than FUra. Despite this potency, numerous laboratories have shown that F-Ade can be used safely as part of GDEPT. Because of 1) strong intratumoral sequestration into cellular nucleic acid, 2) slow release into the systemic compartment following tumor cell death, with uptake by neighboring (bystander) cancer cells in the immediate vicinity, and 3) extensive dilution (throughout the host) of any chemotherapy released from the tumor, the approach leads to safe and consistent antitumor efficacy in numerous animal models in vivo (Ungerechts et al. *Cancer Res.* 2007; 67: 10939-10947; Fu et al. *Cancer Gene Ther.* 2008; 15: 474-484; Parker et al. *Cancer Gene Therapy* 2011 June; 18(6):390-8; Gadi et al. *J. Pharmacol. Exp. Ther.* 2003; 304: 1280-1284; Hong et al. *Cancer Res.* 2004; 64: 6610-6615; Martiniello-Wilks et al. *Human Gene Therapy* 1998; 9: 1617-1626; Mohr et al. *Hepatology* 2000; 31: 606-614; Voeks et al. *Gene Therapy* 2002; 9: 759-768; Martiniello-Wilks et al. *J. Gene Med.* 2004; 6: 1343-1357; Parker et al. *Cancer Gene Therapy* 2003; 10: 23-29; Parker et al. *Human Gene Therapy* 1997; 8: 1637-1644; Martiniello-Wilks et al. *J. Gene Med.* 2004; 6: 43-54; Deharvengt et al. *Int. J. Oncol.* 2007; 30: 1397-1406; Kikuchi et al. *Cancer Gene Ther.* 2007; 14: 279-86). Several direct comparisons between *E. coli* PNP and first generation strategies (HSV-tk and CD) indicate substantial augmentation of GDEPT by a PNP based mechanism (Martiniello-Wilks et al. *Human Gene Therapy* 1998; 9: 1617-1626; et al. *Clin Cancer Res* 1997; 3:2075-80; Nestler et al. *Gene Therapy* 1997; 4:1270-77; Puhlmann et al. *Human Gene Therapy* 1999; 10: 649-657). The approach has recently been approved by the Food and Drug Administration for clinical testing in the United States (IND #14271, approved Mar. 19, 2010).

The prolonged intratumoral half-life of F-Ade metabolites specifically following generation by *E. coli* PNP (>24 hours). (Hong et al. *Cancer Res.* 2004; 64: 6610-6615; Parker et al. *Biochem. Pharmacol.* 1998; 55: 1673-1681; Parker et al. *Cancer Gene Therapy* 2003; 10: 23-29) together with bystander killing of quiescent tumor cells and tumor stem cells (by ablating RNA and protein synthesis), suggested the possible use of PNP as a "point and ablate" modality for concentrating potent chemotherapy within tumor tissues.

Cancer treatments with chemotherapeutic drugs have relied on systemic administration as being equivalent or superior to intratumoral injection. Direct intratumoral injection of a chemotherapeutic is not considered by the conventional prior art as being anymore efficacious than systemic routes in eliciting an antitumor effect because of poor intratumoral uptake, poor tumor cell utilization of the chemotherapeutic, and negligible tumor cell lethality in vivo. Additionally, intratumoral administration is an exacting procedure while systemic administration via intravenous or other systemic route is comparatively simple to perform.

Thus, there exists a need to provide a more effective inhibition therapy against in vivo target cells and in particular tumor cells. There further exists a need to improve a bystander inhibitory effect against target cells and to maintain such effect for a prolonged period.

SUMMARY OF THE INVENTION

The use of a purine nucleoside phosphorylase or nucleoside hydrolase or a vector encoding expression of one of these enzymes is detailed along with the use of a prodrug cleaved by the purine nucleoside phosphorylase or nucleoside hydrolase for the preparation of a direct injection inhibition of replicating or non-replicating targeted cells; the targeted cells normally do not express the introduced purine nucleoside phosphorylase or nucleoside hydrolase. The enzyme and prodrug are amenable to intermixing and injection as a single dose or as separate injections or other administration routes to the targeted cells. Intracellular expression of the enzyme improves efficacy. The use of the inventive substances are particularly effective in the treatment of tumors as a result of a bystander effect in which cells proximal to transfected cells and intercellular fluid containing the enzyme inhibit function or kill cells in contact with the drug released by prodrug cleavage. The substance and prodrug efficacy are enhanced through exposure of the targeted cells to X-ray radiation.

A process for inhibiting replicating or non-replicating targeted cells is also provided that includes the delivery of a purine nucleoside phosphorylase or nucleoside hydrolase to the targeted cells. A prodrug cleaved by the purine nucleoside phosphorylase or nucleoside hydrolase is injected directly into proximity of the targeted cells to release a purine base cytotoxic to the targeted cells so as to kill or inhibit function of the targeted cells. The process is particularly well suited for administration into a tumor. Administration of a prodrug regardless of whether directly into proximity to the targeted cells systemically is effective in combination with X-ray radiation therapy to kill or inhibit function of the targeted cells.

DETAILED DESCRIPTION OF THE PREFERRED EMBODIMENTS

Figure 1:
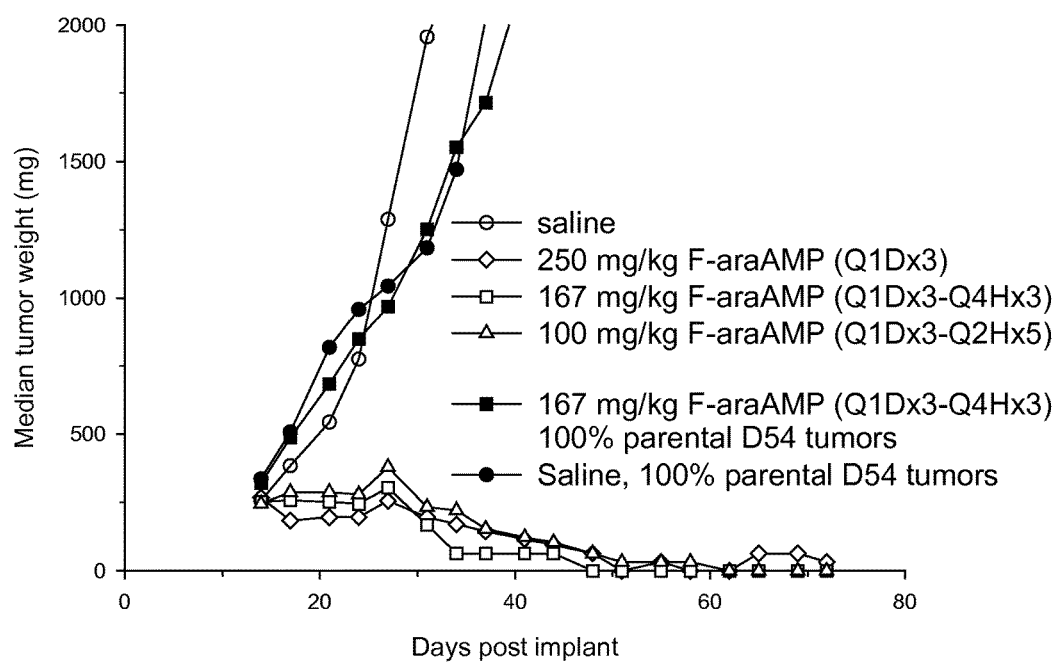
FIG. 1 is a plot of tumor weight as a function of time showing the effect of different schedules of systemic intraperitoneal (IP) fludarabine phosphate (F-araAMP) on D54 tumors that express *E. coli* PNP in 5% of the cells.

The present invention has utility in inhibiting a target cell mass and in a specific embodiment, in vivo tumor growth. It has been surprisingly discovered for direct proximal administration of a prodrug to targeted cells in general and in particular by direct intratumoral injection that upon cleavage by an enzyme, a cytotoxic base is yielded within a targeted cell mass such as a tumor, containing or expressing the enzyme is more efficacious than conventional systemic routes of delivery including orally, parenterally (e.g., intravenously), intramuscularly, intraperitoneally, or transdermally. This is noted to be even more effective when the enzyme is activated intracellularly within the targeted cells.

Direct intratumoral injection of a prodrug has conventionally been discounted as unnecessary and ineffective compared to systemic prodrug delivery owing in part to the well vascularized nature tumors and the other points noted above. Administration of such a prodrug, regardless of administration route, to cells expressing or proximal to the enzyme is rendered more effective when coupled with tumor irradiation. This is considered surprising as PNP or NH are not known to be radiation sensitizers, each enzyme alone, or in the presence of a prodrug substrate.

The present invention is based on injection of a prodrug such as fludarabine phosphate into proximity to target cells expressing non-host purine nucleoside phosphorylase (PNP) or nucleoside hydrolase (NH) resulting in high level bystander inhibition and killing; and destruction of large human tumor xenografts in murine models in vivo. Non-host PNP or NH and prodrug substrate for the enzyme, regardless of the rate of prodrug administration augments radiotherapy and works by a unique mechanism. In particular, intratumoral generation of 2-fluoroadenine or other toxic purine from a prodrug and which is slowly released to the systemic compartment and greatly diluted in the host has improved effect. Injection of large subcutaneous tumors with an adenoviral vector expressing *E. coli* PNP followed by fludarabine phosphate or other prodrugs results in tumor regressions and prolonged inhibition of tumor growth. An anticancer process is provided in which tumors resistant to available agents are safety infiltrated by treatment repetitions (e.g., on a daily basis) to confer 1) trapping of potent chemotherapy within cancer tissue, and 2) destruction of malignant parenchyma in a titratable fashion.

Prolonged target cell inhibition is promoted by direct injection of the prodrug to the target cells in a sustained release formulation. Prolonged release of prodrug promotes inhibition of tumors with a low growth fraction.

An enzyme operative herein is a nonhuman purine nucleoside phosphorylase (PNP) or nucleoside hydrolase (NH) such as that obtained from *E. coli, Trichomonas vaginalis*, or indeed any other nonhuman PNP which can convert a prodrug substrate to produce a cytotoxic purine base. Non-host nucleoside hydrolases along with a suitable prodrug are appreciated to also be operative herein as a basis to practice the present invention. The prodrug, through hydrolase cleavage, is selected to produce a comparatively higher cytotoxicity compound. It is further appreciated that mutant PNPs and hydrolases such as those detailed in U.S. Pat. No. 7,488,598 are operative herein to generate a cytotoxic purine base from the prodrug and suitable for inhibiting cellular function such as reproduction and even killing of those cells of a human subject that have been transfected or are simply in proximity to the enzyme. It is appreciated that an enzyme as used herein affords a cytotoxic purine base of sufficient potency to generate a bystander effect thereby inhibiting transfected cells, transduced cells, as well as bystander cells.

As used herein "proximity" is intended to mean introduction directly into a defined tissue mass, such as for example a tumor mass, as well as adjacent to a target cell within a spacing of approximately 50 adjacent cell diameters or equivalent linear spacing and preferably within 20 adjacent cell diameters or equivalent linear spacing.

A prodrug operative herein has the attribute of being relatively nontoxic to subject cells yet upon enzymatic cleavage of the prodrug produces a cytotoxic purine base. Representative prodrugs are known to the art (Ungerechts et al. *Cancer Res.* 2007; 67: 10939-10947; Fu et al. *Cancer Gene Ther.* 2008; 15: 474-484; Fu et al. *Cancer Sci.* 2008; 99: 1172-1179; Parker et al. *Cancer Gene Therapy* In press; Gadi et al. *J. Pharmacol. Exp. Ther.* 2003; 304: 1280-1284; Hong et al. *Cancer Res.* 2004; 64: 6610-6615; et al. *Biochem. Pharmacol.* 1998; 55: 1673-1681; Martiniello-Wilks et al. *Human Gene Therapy* 1998; 9: 1617-1626; Mohr et al. *Hepatology* 2000; 31: 606-614; Voeks et al. *Gene Therapy* 2002; 9: 759-768; Martiniello-Wilks et al. *J. Gene Med.* 2004; 6: 1343-1357; Parker et al. *Cancer Gene Therapy* 2003; 10: 23-29; Parker et al. *Human Gene Therapy* 1997; 8: 1637-1644; Martiniello-Wilks et al. *J. Gene Med.* 2004; 6: 43-54). While the following data details the operation of the present invention in the context of F-dAdo and F-araAMP, it is appreciated that these results are extendable to other prodrugs.

A D54 human glioma model is selected to investigate safety and efficacy of *E. coli* PNP/F-araAMP for several reasons. First, D54 tumors in mice are refractory to conventional chemotherapeutic agents, including compounds such as BCNU that are clinically approved for human glioma treatment. Second, the D54 model is relatively slow growing in mice (doubling time of 10 to 15 days), and provides a means to test whether an approach kills both dividing and nondividing tumor cells. Because F-araAMP administration schedules described below are given over a three-day period, complete regression or cure establishes destruction of the non-proliferative compartment of a tumor mass. Third, human gliomas have been a target for clinical testing of GDEPT. Human D54 tumors are highly resistant to conventional chemo-, radio-, and gene therapy-based interventions. It should be noted that although a glioma model is selected for the present analysis, the established mechanism of cell killing by purine bases such as F-Ade or other prodrugs (disruption of RNA and protein synthesis) is active against diverse malignant cell types. (Parker et al. *Biochem. Pharmacol.* 1998; 55: 1673-1681). The experiments below describe ablation of quiescent tumor cells following either lentiviral transduction or adenoviral gene delivery. It is appreciated that other tumors including DU145, as well as numerous other gene transfer vectors and prodrug substrates for encoded enzymes are operative herein.

To explore the breadth and efficacy of the inventive therapy, the NCI-H322M non-small cell lung adenocarcinoma cell line is also studied. Conventional chemotherapy and radiotherapy protocols afford sufferers of this cancer a five year survival of less than 15%. NCI-H322M shares many of the attributes of D54 human glioma in that the tumors are generally refractory to conventional therapies. The ability of the present invention to kill both dividing and non-dividing NCI-H322M cells demonstrates the generality of the claimed invention being able to kill or otherwise inhibit cellular function in a variety of target cells types.

The present invention details a process for generating a very potent cytotoxic agent specifically within a target cell volume in general and specifically in tumor parenchyma. The inventive strategy has been shown safe based on the limited radius of F-Ade diffusion following generation within a tumor mass and extensive dilution (to unmeasurable F-Ade levels in serum) after release from dying tumor cells and confers consistent in vivo bystander killing. The inventive mechanism of antitumor activity also differs fundamentally from all other approaches to GDEPT. Antitumor activity of F-Ade is due to disruption of RNA and protein synthesis, which causes ablation of both dividing and non-dividing tumor cells. (Parker et al. *Biochem. Pharmacol.* 1998; 55: 1673-1681.) The finding that relatively slow growing D54, NCI-H322M, or DU145 tumors are reduced in mass by three days of intratumoral treatment (see in particular FIG. 2C, as well as FIGS. 5A, 5B, and 7B) indicates activity against both cycling and noncycling tumor cells in vivo.

Intratumoral injection of F-araAMP of the present invention minimizes systemic exposure to the prodrug and maximizes drug levels within the target cell mass such as a tumor tissue itself. Pronounced antitumor activity following intratumoral injection of F-araAMP or other prodrugs is noted in the setting of PNP or NH expression. The combination of Ad/PNP with intratumoral F-araAMP injection is noted herein to be significantly more efficacious than Ad/PNP followed by systemic F-araAMP according to the present invention. It is noted that prodrug injection is effective when administered in a single bolus with PNP or NH, or in injections temporally displaced relative to the non-human PNP or NH enzyme presence in the parenchyma.

These results suggest a straightforward means for applying a comparable strategy in human subjects and without the need for modification of vector tropism, enhanced bystander killing, or retargeting. Both the adenoviral vector and F-araAMP have been comprehensively studied in previous clinical trials. Moreover, the doses of F-araAMP given as local therapy to treat 300 mg tumors in mice (3 to 24 mg administered 3 times) are much less than the amount of F-araAMP routinely administered as part of standard clinical care in humans (~40 mg per dose×5 daily doses given every 4 weeks). The present invention provides a therapeutic modality in which Ad/PNP followed by F-araAMP are administered repeatedly to needle-accessible tumors (prostate, breast, head and neck, or with radiology guidance, other tumor masses) on a frequent (e.g., daily) basis to sequentially destroy large regions of a tumor while minimizing systemic exposure to either F-araAMP, F-Ade, or other PNP cleaved prodrug. A "point and ablate" approach is feasible specifically for the PNP GDEPT approach because of the potent antitumor activity of F-Ade and its high bystander activity, together with activity against nonproliferating tumor cells. Intratumoral generation of F-Ade should provide a means to concentrate the agent intratumorally and minimize systemic exposure in the host.

Radiotherapy primarily targets actively dividing tumor cells, but fails to ablate quiescent tumor tissues, particularly in areas of necrosis (Puhlmann et al. *Human Gene Therapy* 1999; 10: 649-657). The present invention provides an enhancement of radiotherapy in combination with PNP or NH prodrug. Very potent anticancer agents that work through a mechanism distinct from XRT are provided herein to treat the non-cycling compartment of solid malignancies. F-Ade, which potently kills both dividing and nondividing tumor cells, is a preferred compound in this regard. Common tumors that are administered radiation therapy prior to surgical resection (glioma, breast, prostate, head & neck, lung, and other cancers treated with curative or palliative intent) also benefit from an inventive combination therapy.

In the method of the invention described above, the mammalian cells to be killed can be tumor cells. Cells comprising any solid tumor, whether malignant or not, can be killed by the present method based on the ability to transfer or express the PNP or NH gene selectively to at least a small percentage of cells comprising the tumor. For example, it has been shown that intravenous injection of liposome carrying DNA can mediate targeted expression of genes in certain cell types. Targeting of a PNP or NH gene or expression of the gene to a small fraction of the cells in a tumor mass followed by substrate administration could be adequate to mediate involution. (Zhu et al. *Science* 261:209-211, 1993) Through the substantial bystander effect and killing of nondividing cells demonstrated in the Examples, the present method can destroy the tumor. Although, in the exemplified method, the mammalian cells are human glioma, non-small cell lung adenocarcinoma, or prostate cells, it can be appreciated that the methods taught herein can be applied to other cells and their susceptibility to the present methods can be determined as taught.

In addition to killing tumor cells, the method of the invention can also kill virally infected cells. In a virus-killing embodiment, the gene transfer method selected would be chosen for its ability to target the expression of PNP in virally infected cells. For example, virally infected cells may utilize special viral gene sequences to regulate and permit gene expression (i.e., virus specific promoters). Such sequences are not present in uninfected cells. If *E. coli* or other PNP genes are oriented appropriately with regard to such a viral promoter, PNP would only be activated within virally infected cells, and not other, uninfected, cells. In this case, virally infected cells would be much more susceptible to the administration of F-araAMP, MeP-dR or other substrates designed to be converted to toxic form by PNP or NH when delivered in proximity to target cells.

In other applications of the present invention, a medicament is provided to kill or otherwise inhibit the function of any desired target cell volume of a subject. The broad applicability of the present invention to kill or otherwise inhibit function of cells affords clinical practitioners with superior control of administration, as well as improved healing profiles over a variety of conventional procedures. The present invention affords a chemical cellular ablation alternative to procedures involving cautery, excision. It has been surprisingly noted that the chemical cellular ablation afforded by the present invention precludes the granulation and scarification associated with cautery, radioablation, or excision techniques thereby providing a superior healed tissue around the situs of chemical ablation and as a result, the present invention has uses in the treatment of cardiac arrhythmia, cyst reduction, ganglion treatment, male sterilization, cosmetic dermatological procedures, and melanoma treatment. It is appreciated that chemical cellular ablation according to the present invention is readily performed by administration of PNP or NH enzyme, genes expressing any form of a viral vector as detailed herein; along with proximal delivery of a prodrug for the PNP or NH. Based on the location of the target cells for chemical cellular ablation, inventive medicament is administered via a catheter, microsyringe, canula, or syringe; as well as topically in a cream base. Preferably, the PNP or NH enzyme is expressed intracellularly.

An isolated nucleic acid encoding a non-human or genetically modified human purine nucleoside phosphorylase or nucleoside hydrolase in a mammalian cell is provided in the present invention. More specifically, the invention provides an isolated nucleic acid encoding an E. coli PNP in a mammalian cell. By "isolated" is meant separated from other nucleic acids found in the naturally occurring organism from which the PNP gene is obtained.

As described above, in a preferred embodiment, the PNP or NH used in the present methods can include genetically modified human or nonhuman mammalian PNP or NH capable of reacting with a substrate that the native PNP or NH in the cell to be killed will not recognize or recognizes very poorly. Thus, the nucleic acids of the invention that encode the PNP or NH of the invention are present in cells in which they are not naturally found, either because they are from a different organism or because they have been modified from their natural state. The key requirements of the nucleic acids encoding the PNP or NH is that they must encode a functional enzyme that is able to recognize and act upon a substrate that is not well recognized by the native PNP or NH of the cell.

A eukaryotic transfer vector comprising a nucleic acid encoding a non-human or genetically modified purine nucleoside phosphorylase or nucleoside hydrolase is also provided. The vector must be capable of transducing or transfecting at least some percentage of the cells targeted. The transfer vector can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, 1993). The Examples provide a lentiviral or adenoviral vector containing a nucleic acid encoding PNP.

The vector of the invention can be in a host capable of expressing a functional PNP or NH. As used in the method of the invention, the host cell is the cell to be killed, which expresses the PNP or NH and is killed by the toxic product of the reaction of the enzyme and the prodrug that is an enzymatic substrate. A method of determining susceptibility is provided in the Examples which teach protocols for the transfection of host cells, and demonstrate the expression of PNP and toxicity to the host cells in the presence of substrate. Alternatively, the active enzyme or pro-enzyme thereof is administered into a target cell mass.

In addition to the present gene transfer methods, the PNP gene product can also be selectively delivered to the tumor cells by a number of different mechanisms and this PNP could be used to produce F-Ade at the site of the tumor.

For instance, the PNP or NH enzyme can be attached to any desired monoclonal antibody and injected into the patient either systemically or into proximity to target cells. After allowing sufficient time for the clearance of all PNP or NH conjugated to monoclonal antibody that has not bound to the target cells, the patient is treated with by direct injection of the prodrug, such as F-araAMP, which is cleaved to F-Ade only at the targeted site. Such a procedure requires only the availability of an appropriate monoclonal antibody. The procedures used for conjugating proteins to target-specific monoclonal antibodies are routinely available. The following references are examples of the use of this technology to target specific proteins to tumor tissue (Senter et al. *Bioconjugate Chem.* 2:447-451, 1991; Bagshawe et al. *Br. J. Cancer* 60:275-281, 1989; Bagshawe et al. *Br. J. Cancer* 58:700-703, 1988; Senter et al. *Bioconjugate Chem.* 4:3-9, 1993; Battelli et al. *Cancer Immunol. Immunother.* 35:421-425, 1992; Pietersz and McKenzie *Immunolog. Reviews* 129:57-80, 1992; and Roffler et al. *Biochem. Pharmacol* 42:2062-2065, 1991). Other ligands, in addition to monoclonal antibodies, can be selected for their specificity for a target cell and tested according to the methods taught herein.

It is also possible to entrap proteins in liposomes and target them to specific tissues. The PNP or NH gene product can, thus, be selectively delivered to a tumor mass using targeted liposomes. After all non-targeted liposome is cleared from the blood, the patient is treated with F-araAMP which is cleaved to F-Ade by the PNP only at the targeted site. Once again, this procedure requires only the availability of an appropriate targeting vehicle. The following references are examples of the use of this technology to target specific proteins to tumor tissue (Hughes et al. *Cancer Research* 49:6214-62210, 1989; and Litzinger and Huang *Biochimica et Biophysica Acta* 1104:179-187, 1992).

A prodrug that represents enzymatic substrate for a non-host PNP or NH is injected directly into target cell mass as for example, intratumorally in a pharmaceutically acceptable carrier such as for example saline or DMSO, or alternatively, is encapsulated to modify prodrug stability and/or therapeutic characteristics. An inventive prodrug is readily administered as a gel, paste or capsulated within microparticles. It is appreciated that such carriers for prodrugs are readily used to provide a prolonged release of the prodrug, modified diffusion within the targeted cell mass, and storage stability as compared to dissolution in a saline solution. With resort to microparticles, release rates of an inventive prodrug are readily extended to more than one week, more than two weeks, even beyond six weeks. (Zentner et al., *J. control release* 72 (1-3): 203-215, 2001). An inventive prodrug is readily prepared and injected in a paste of polylactic acid, poly(epsilon-caprolactone), or a combination thereof (Jackson et al., *Cancer research* 60 (15): 4146-4151, 2000). Prodrugs are also suitably encapsulated within microspheres from a variety of materials including polylactic acid, poly(epsilon-caprolactone), polyvinyl pyrrolidone, hydroxypropylcellulose, methyl cellulose, and other polysaccharides (Harper et al, *Clin. Canc. Res.* 5:4242-4248, 1999; Dordunno et al., *Cancer Chemother. Pharmacol.* 36: 279-282, 1995; Bert et al., *Cancer Lett.* 88:73-78, 1995;) It is appreciated that with a controlled release formulation of prodrug, larger dosings of prodrug are injected into a target cell mass less frequently to achieve a prolonged cell inhibition and bystander effect.

Injection of the enzyme and prodrug into a target cell volume such as a tumor, can be performed for monetary compensation, with the subject having an undesired growth or function of targeted cells compensating a provider of injection according to the present invention for the effort of inhibiting function or even killing the target cells.

The present invention is further detailed with respect to the following nonlimiting examples. These examples are not intended to limit the scope of the appended claims.

EXAMPLES

Example 1. Studies with Human Tumor Xenografts in Mice

Parental and *E. coli* PNP expressing D54MG (human glioma) tumor cells ($2\times10^7$ cells) are injected subcutaneously into the flanks of nude mice (nu/nu) purchased from Charles River Laboratories (Wilmington, Mass.). D54 tumor cells stably transduced with *E. coli* PNP are prepared as described previously (Parker et al. *Cancer Gene Therapy* 2011 June; 18(6):390-8). Tumors are measured with calipers and an estimate of the weight calculated using the equation, (length×width$^2$)/2=mm$^3$, and converted to mg assuming unit density. Unless stated otherwise, therapeutic drugs and the adenoviral vector expressing *E. coli* PNP (Ad/PNP) are injected into D54 tumors in 150 µl volumes by 8 separate injections of approximately 20 µl each in an effort to evenly distribute the administered agent. Each treatment arm of each group contained at least 6 mice. Mice are monitored daily for weight loss and twice weekly for tumor dimensions. T-C (tumor growth delay) is taken as the difference in days to 2 doublings between drug-treated and saline-treated groups. The time to the evaluation point for each animal (2 doublings) is used as the end point in a Student's t-test, the Mann-Whitney rank sum test, or a life table analysis in order to statistically compare growth data between treatment groups. All procedures are performed in accordance with a protocol approved by the IACUC of Southern Research Institute. F-araAMP is obtained from Schering A.-G. (Berlin, Germany). In this and subsequent examples, F-Ade is obtained from General Intermediates of Canada, Inc. (Edmonton, Alberta, Canada). Treatments are initiated when tumors are 250 to 300 mg (~1-1.5% of total animal weight).

Example 2. Measurement of *E. coli* PNP Activity

The proportion of lentiviral transduced cells in a tumor mass is verified by measuring *E. coli* PNP activity in representative cancers removed from mice on the first day of drug treatment. Crude extracts are prepared as described previously (Parker et al. *Human Gene Therapy* 1997; 8: 1637-1644) after tumor excision from the flanks of mice. The extracts are incubated with 50 mM PO$_4$, 100 µM 6-methylpurine-2'-deoxyriboxide (MeP-dR), and 100 mM HEPES buffer (pH 7.4) at a concentration of extract that resulted in a linear reaction over the incubation period. The formation of MeP is monitored using reverse phase HPLC. By convention, one unit of PNP activity is defined as the amount of extract necessary to cleave 1 nmole of MeP-dR per mg protein in a 1 hour period.

Example 3. Monitoring Intratumoral Metabolism of F-araAMP

Total radioactivity is determined after injection of 3 mg [8-$^3$H]F-araAMP (10 µCi) into 300 mg D54 flank tumors. [8-$^3$H]F-araAMP is obtained from Moravek Biochemicals Inc. (Brea, Calif.). Tumors are removed from the mice at 10 minutes or 4 hours after injection and dissolved in 1 ml of Soluene 350 (Packard Instrument, Meriden, Conn.) by incubating at 55° C. for 4 hours. A portion of each extract is mixed with scintillation fluid and radioactivity determined.

Example 4. Effect of Different Schedules of Fludarabine Phosphate (F-araAMP) on D54 Tumors that Express *E. coli* PNP in 5% of the Cells Parental D54 tumor cells are mixed with D54 tumor cells stably transduced with *E. coli* PNP by a lentivirus so that 5% of the mixture expressed the PNP transgene. This 95/5 mixture is injected sc into the flanks of nude mice. Intraperitoneal treatment with F-araAMP (250 mg/kg once per day for 3 consecutive days; 167 mg/kg 3 times per day for 3 consecutive days; 100 mg/kg 5 times a day for 3 consecutive days; or vehicle control 5 times a day×3 days) began on day 17 when tumors are approximately 250 mg. The activity of *E. coli* PNP in the tumors at the time of treatment (day 17) is 2,500±400 units. Tumor growth in all F-araAMP treatment groups is significantly different than that in vehicle treated group P<0.001. (FIG. 1)

FIG. 1 depicts the antitumor activity of *E. coli* PNP plus fludarabine phosphate (F-araAMP) when 5% of tumor cells (transduced with the gene prior to implantation) express the recombinant enzyme. Intraperitoneal (systemic) administration of F-araAMP (100 mg/kg given 15 times, 167 mg/kg given 9 times, or 250 mg/kg given 3 times) leads to complete regressions of all tumors and cures of all mice. It has been shown previously that parental D54 tumors (i.e. without *E. coli* PNP) are not sensitive to treatment with F-araAMP and that tumor regressions with F-araAMP in this setting exhibit dose dependence on the fraction of tumor cells expressing *E. coli* PNP (Hong et al. *Cancer Res.* 2004; 64: 6610-6615; Parker et al. *Human Gene Therapy* 1997; 8: 1637-1644; also see below). Tumors in which 100% of cells are transduced with *E. coli* PNP and non-transduced (parental) tumors grow at similar rates (Hong et al. *Cancer Res.* 2004; 64: 6610-6615), suggesting that a ~5% level of transduction would be maintained throughout expansion of the tumor model. To verify this assertion, tumor extracts are prepared from three representative tumors taken from mice on the first day of drug treatment and levels of *E. coli* PNP determined to be 2,500±400 units. *E. coli* PNP activity of 126,000 units is present in tumors comprised of 100% PNP expressing cells from this cell line (Hong et al. *Cancer Res.* 2004; 64: 6610-6615). The findings therefore suggest that in this particular experiment the parental (no PNP-expression) cells grew slightly more rapidly than the PNP transduced line in vivo, and confirm that transduction percentage described in FIG. 1 is ≤5%, and perhaps closer to 2-3%.

The results shown in FIG. 1 establish that complete regressions or cures of large tumors (approximately 1% of the total body weight of the animal) can be safely accomplished by an intraperitoneal PNP-based GDEPT strategy. The findings also demonstrate excellent in vivo bystander activity. As few as three intraperitoneal (IP) injections of F-araAMP instant (non-sustained release) leads to destruction of large tumors, although ≤5% of cells express the activating gene. Moreover, treatment with F-araAMP results in only a 10 to 20% decrease in body weight, which is quickly regained after the F-araAMP schedule is completed. There is no gross tissue damage in the region immediately surrounding the tumor or other evidence of undesired sequelae despite a substantial prolongation of life. A single IP injection of 3× dose F-araAMP 30% by weight in polylactic acid microspheres achieves a similar effect.

Example 5. Intratumoral Injection of F-araAMP on D54 Tumors

Figure 2A:
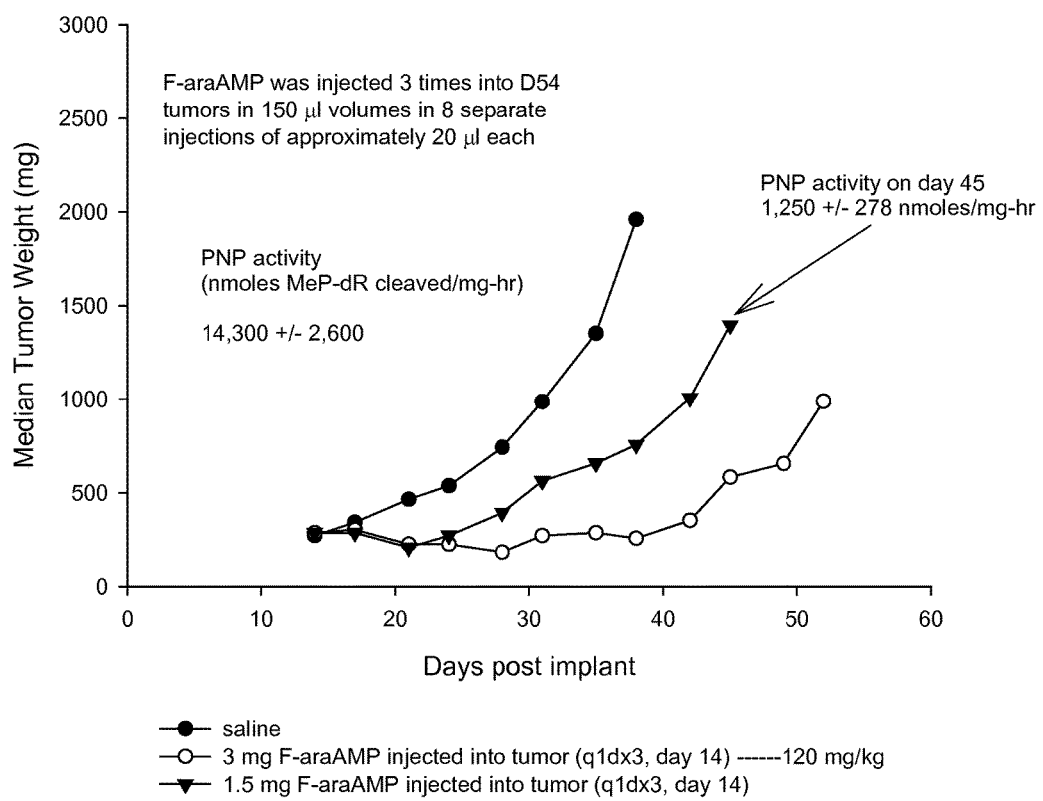
FIG. 2A is a plot of tumor weight as a function of time showing the effects of intratumorally injected F-araAMP into tumors that express *E. coli* PNP in 10% of their cells and resulting in antitumor activity.
Figure 2B:
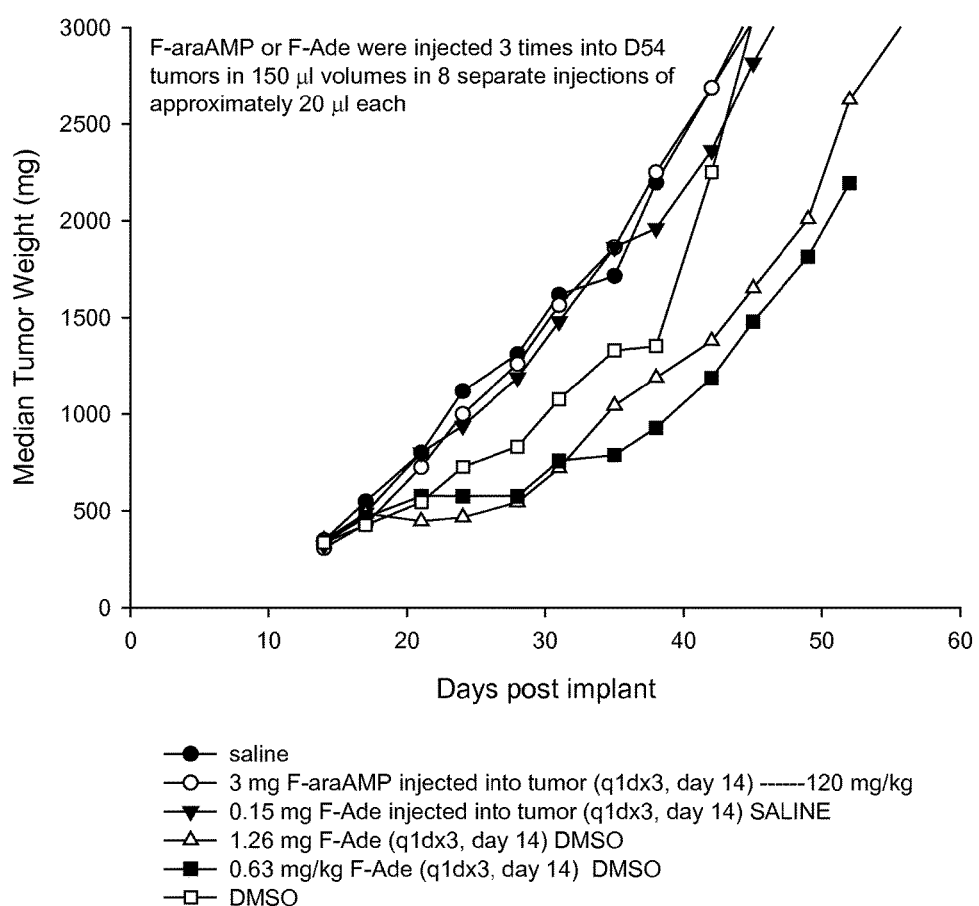
FIG. 2B is a plot of tumor weight as a function of time showing the effect of intratumoral injection of F-araAMP at high concentrations in D54 tumors where none of the cells express *E. coli* PNP activity.

In FIG. 2A, parental D54 tumor cells are mixed with D54 tumor cells that had been transduced with E. coli PNP to a final proportion in which 10% express the transgene. This 90/10 mixture is injected sc into the flanks of nude mice. Tumors are injected once per day for 3 consecutive days starting on day 14 with 150 µl of saline, 1.5 mg of F-araAMP dissolved in saline, or 3 mg of F-araAMP is dissolved in saline. The activity of E. coli PNP in the tumors at the time of treatment (day 14) is 14,300±2,600 units. Tumor growth in the 3 mg treatment group is significantly different than that in the vehicle treated group (P<0.001) but is not significantly different than that in the 1.5 mg treatment group (P=0.458). In FIG. 2B, parental D54 tumor cells (no E. coli PNP expression) are injected sc into the flanks of nude mice. Tumors are inoculated once per day for 3 consecutive days starting on day 14 with 150 µl of saline, 3 mg F-araAMP is dissolved in saline, 0.15 mg of F-Ade dissolved in saline, 1.26 mg of F-Ade dissolved in 150 mL DMSO, 0.63 mg of F-Ade dissolved in DMSO, or DMSO. This experiment is repeated with a single injection of 9 mg F-araAMP 30% by weight in polyactic acid microspheres in saline with similar results. The tumor growth in mice treated with 0.63 or 1.26 mg F-Ade dissolved in DMSO is significantly different than that in the DMSO vehicle treatment group (P=0.011 and 0.002, respectively).

Figure 2C:
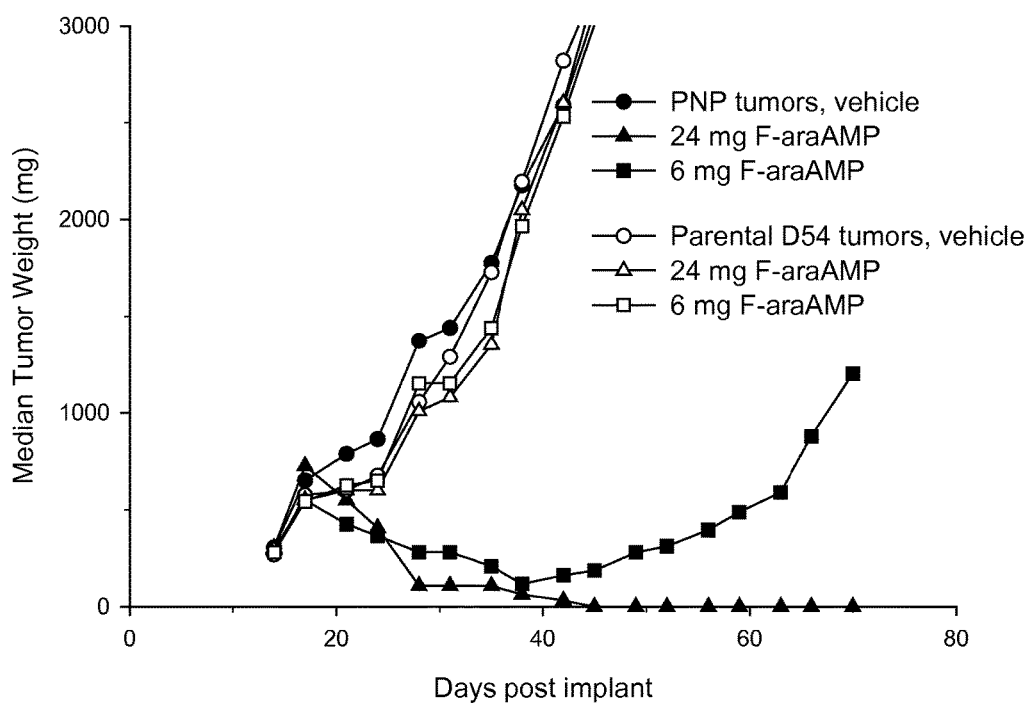
FIG. 2C is a plot of tumor weight as a function of time showing the effect of F-araAMP injection into tumors on D54 tumor growth in which 10% of the cells express *E. coli* PNP activity.

In FIG. 2A, it is shown that injection of F-araAMP into tumors in which 10% of the cells express E. coli PNP has a strong antitumor effect. Note that the dose of F-araAMP in this experiment is considerably below the maximally tolerated dose and that additional injections are made with greater antitumor activity. In the low dose of F-araAMP, the PNP activity in the tumors 45 days after treatment with F-araAMP is 1,250 units, whereas at the time of treatment the PNP activity in the tumors is 14,300 units. This result indicates that the F-araAMP treatment preferentially killed cells expressing E. coli PNP, which suggests that the antitumor activity is dependent on the expression of E. coli PNP. The amount of F-araAMP injected is 120 mg/kg which is much less than the maximally tolerated dose at this schedule (750 mg/kg, q1d×3). Better results are seen at higher doses of F-araAMP when dissolved in DMSO; FIG. 2C.

Figure 2D:
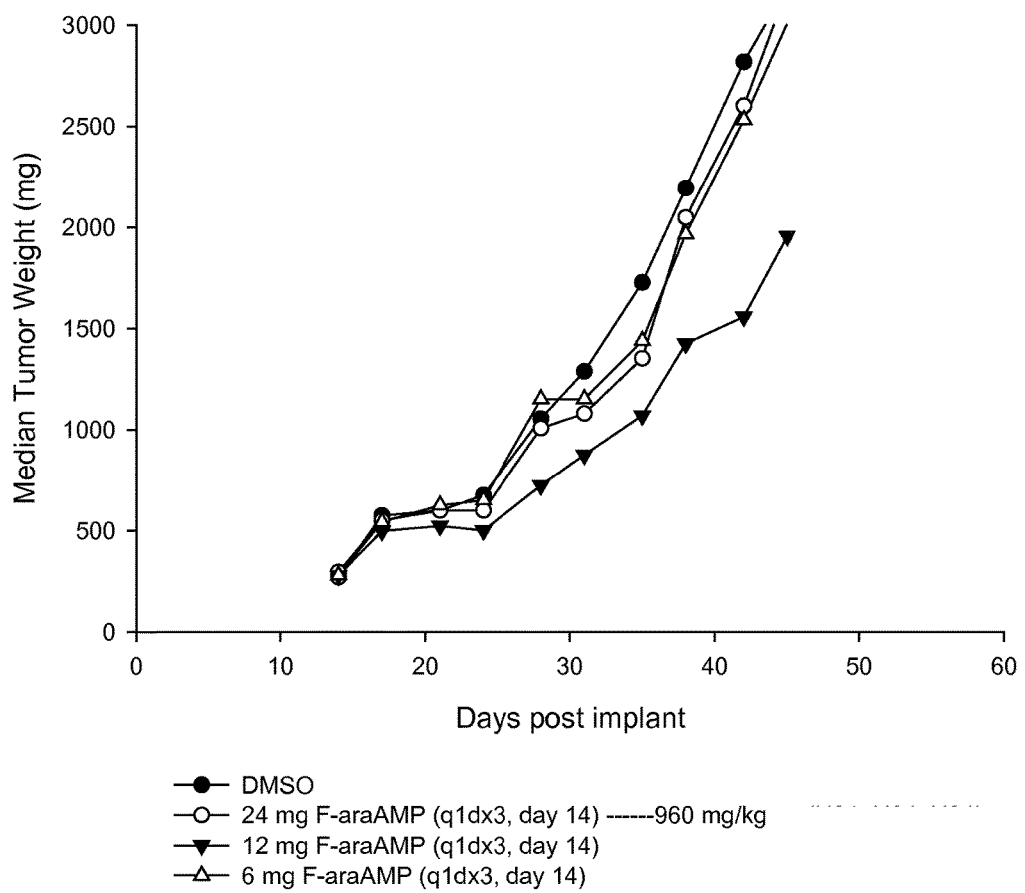
FIG. 2D is a plot of tumor weight as a function of time showing the effect of F-araAMP injection into tumors on D54 tumor growth where none of the cells express *E. coli* PNP activity.
Figure 3:
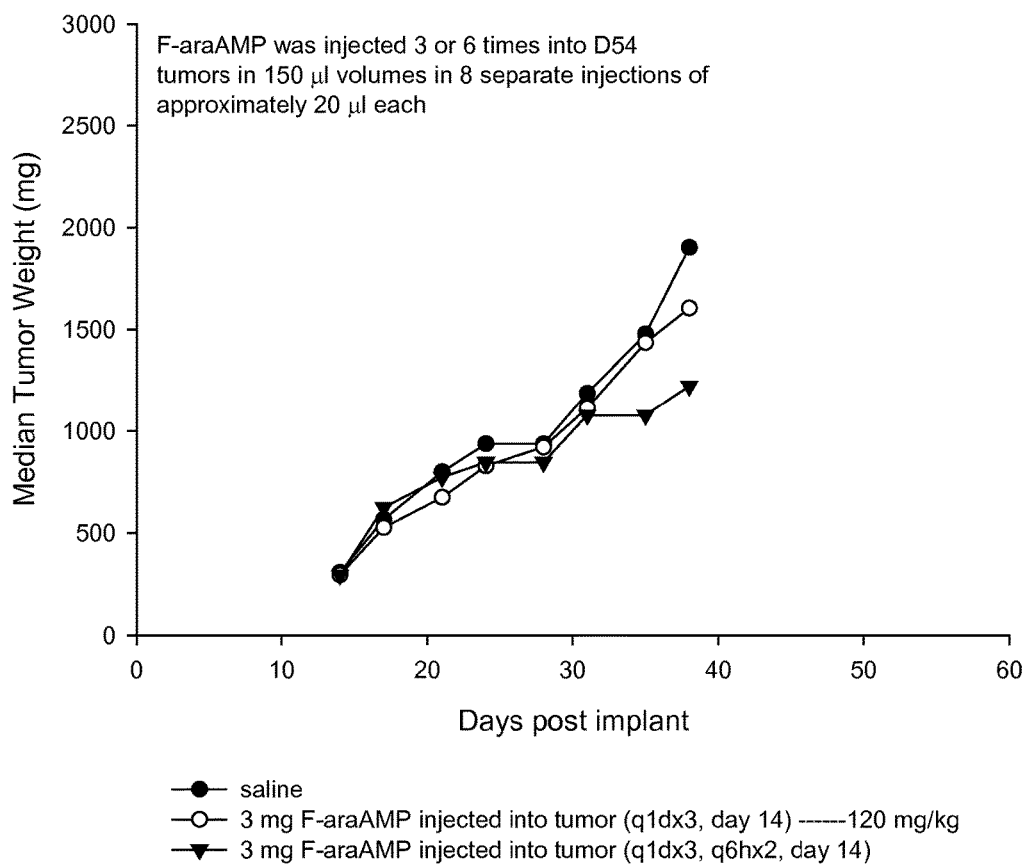
FIG. 3 is a plot of tumor weight as a function of time showing that direct intratumoral injection of F-araAMP (once per day or twice per day) into tumors that do not express *E. coli* PNP has no effect on tumor growth.
Figure 4:
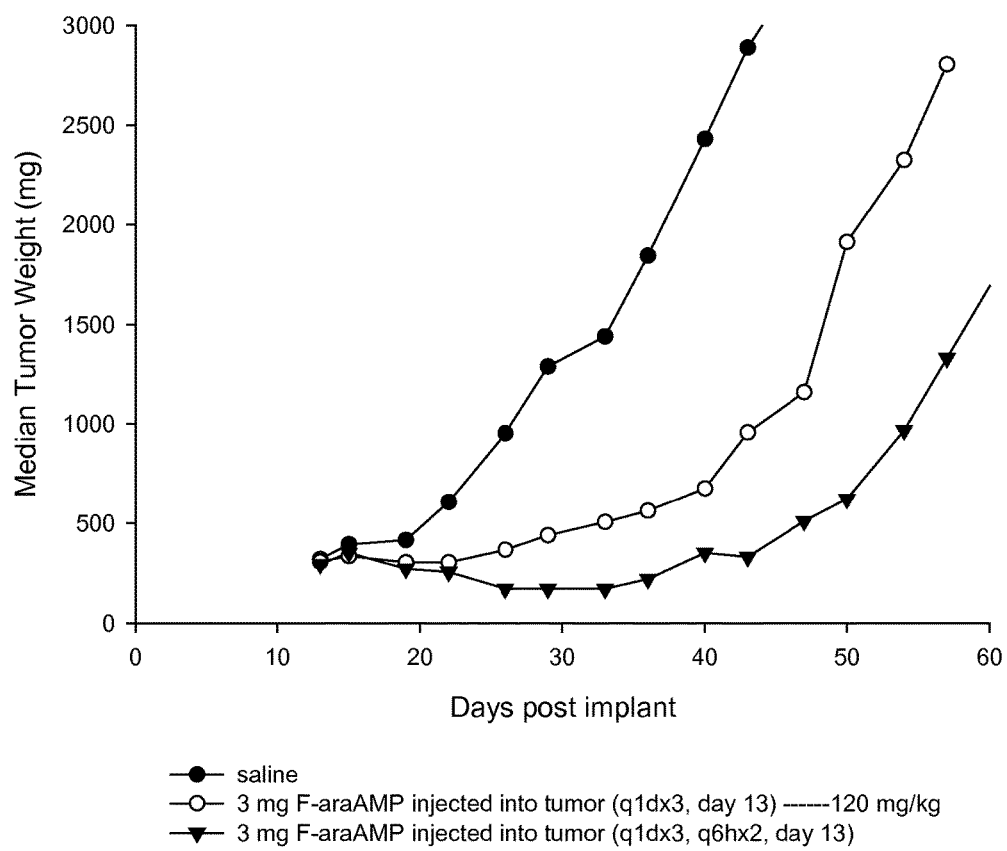
FIG. 4 is a plot of tumor weight as a function of time showing that direct intratumoral injection of F-araAMP into tumors that express *E. coli* PNP in 10% of their cells results in very good antitumor activity, with six injections being better than three injections.

Example 6. Intratumoral Injection of F-araAMP in D54 Tumor Cells with and Without PNP In FIGS. 2B, 2D and 3 it is shown that direct intratumoral injection of F-araAMP into tumors in which no cells express E. coli PNP activity has no effect of tumor growth. This result indicates that the antitumor activity of F-araAMP shown in FIGS. 2A, 2C and 4 is due to the expression of E. coli PNP in a subset of the tumor cells. The antitumor activity of F-Ade (the active metabolite of F-araAMP) is also injected into tumors in the same manner as F-araAMP. 0.15 ml of 1 mg/ml F-Ade dissolved in water (limit of solubility) shows no antitumor effect. 0.15 ml of 8.6 mg/ml F-Ade dissolved in DMSO is injected into tumors; a modest antitumor effect is observed.

These results indicate that a product containing both a vector (to deliver E. coli PNP) and time-released F-araAMP is effective in the treatment of local cancers that otherwise are untreatable. At least one injection of this product would inhibit metabolism or even kill any cell that expresses E. coli PNP plus many bystander cells with reduced systemic toxicities associated with F-araAMP. This is repeated as many times as necessary to abolish a tumor mass. For example, a patient is injected once per week on an outpatient basis with reduced toxicity until the tumor is completely eliminated. Multiple intratumoral injections of F-araAMP resulted in greater antitumor activity (FIG. 4).

Since only a fraction of F-araAMP injected IP actually perfuses a malignant tumor in vivo, it is tested whether injecting F-araAMP directly into the tumor mass could enhance efficacy. An initial study is shown (and introduced above) for tumors in which 10% of cells expressed E. coli PNP (FIG. 2A). Intratumoral injection of 3 mg of F-araAMP per injection (3 total injections) confers significant antitumor effects (p<0.001 with little or no weight loss (less than 4%); whereas F-araAMP has no effect when injected into parental (no E. coli PNP expressing) tumors (FIG. 2B). Because the weight of a mouse is approximately 0.025 kg, injection of 3 mg F-araAMP is equivalent to a dose of 120 mg/kg F-araAMP, which is 25 to 50 percent of the total systemic amounts studied in FIG. 1. Injection of F-Ade (the active metabolite of F-araAMP) into tumors also fails to elicit antitumor activity when tested at the highest possible solubility in saline (FIG. 2B). F-Ade is also dissolved in DMSO, and three injections of 1.26 mg F-Ade (the approximate molar equivalent of F-Ade in a 3 mg injection of F-araAMP) into the tumor resulted in minimal antitumor activity (FIG. 2B; p=0.011 with respect to mice injected with DMSO vehicle), but caused a 10% decrease in body weight. Three intratumoral injections of either 2.5 or 5 mg of F-Ade (dissolved in DMSO) led to death in 3 of 6 and 4 of 6 mice, respectively, which indicated that 1.26 mg is very near its maximally tolerated dose (MTD). The results therefore demonstrate that unlike IT F-araAMP following intratumoral expression of E. coli PNP, direct IT injection of F-Ade has little antitumor efficacy.

As noted above, the amount of F-araAMP given intratumorally (in FIG. 2A) is less than the total intraperitoneal dose described in FIG. 1. In order to investigate the impact of higher doses of F-araAMP, the F-araAMP is dissolved in DMSO, and given at concentrations well tolerated IT, but well above the maximally-tolerated dose if administered IP (Hong et al. Cancer Res. 2004; 64: 6610-6615). Three doses of 6 or 24 mg is administered by IT injection to tumors in which 10% of cells expressed E. coli PNP (FIG. 2C). Parental D54 tumor cells or mixtures of D54 tumor cells in which 10% of the cells express E. coli PNP are injected sc into the flanks of nude mice. Tumors are injected once per day for 3 consecutive days starting on day 17 with 150 µl of DMSO, 24 mg F-araAMP in DMSO, or 6 mg F-araAMP in DMSO. The activity of E. coli PNP in the D54 tumors in which 10% of the cells express E. coli PNP (on day 17) is 8,600±620 units. The tumor growth in the mice bearing PNP tumors and treated with 6 or 24 mg of F-araAMP is significantly different than the vehicle treated group (P=0.014 and <0.001, respectively), but is not significantly different from one another in this experiment. Three of the 6 tumors treated with 24 mg of F-araAMP became ulcerated (days 17, 21, and 24), requiring sacrifice of the study animals. The remaining 3 tumors completely regressed and mice remained tumor-free until the experiment is ended on day 70. There are no ulcerations in tumors treated with 6 mg of F-araAMP, and a single course of this treatment led to robust tumor regressions and a prolonged antitumor effect. Injection of F-araAMP at the highest dose resulted in a modest (7%) decrease in body weight, which recovered rapidly following completion of drug treatment. Injection of F-araAMP at these doses into parental tumors (no PNP-expression) did not result in antitumor activity.

Example 7. Effect of Intratumoral F-araAMP and Ad/PNP on D54 Tumors

Figure 5A:
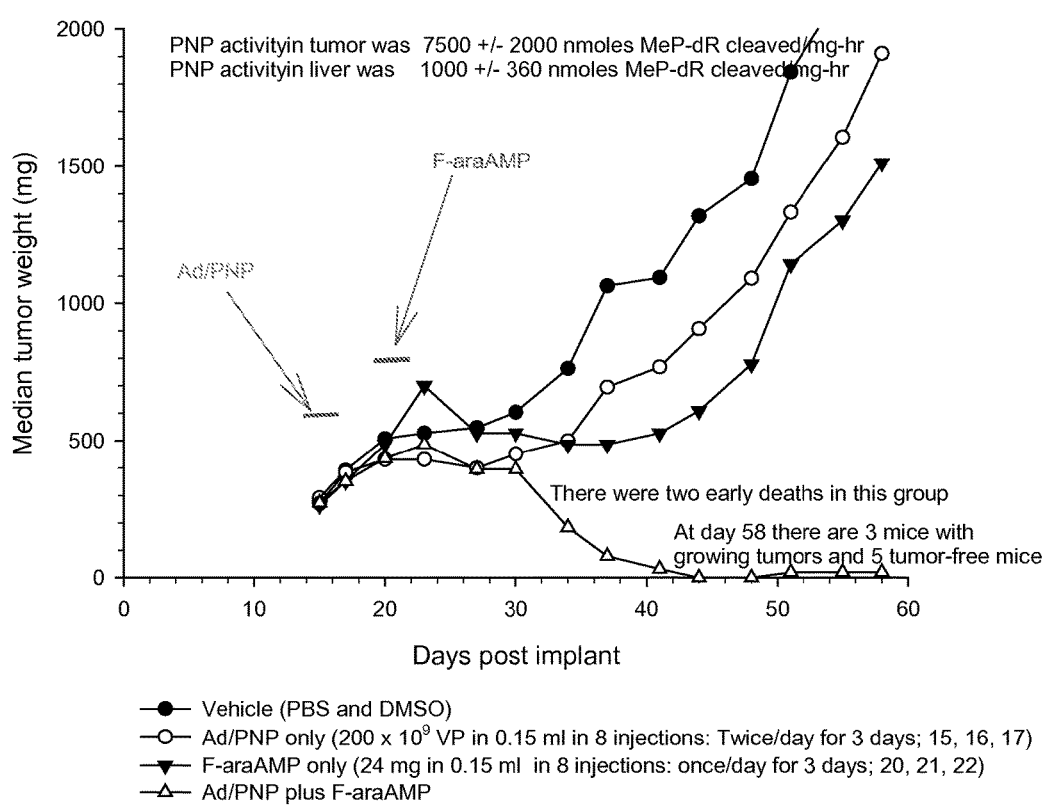
FIG. 5A is a plot of tumor weight as a function of time showing the effect of adenoviral vector (Ad) PNP plus F-araAMP on D54 tumors at a high F-araAMP dosing regime of 24 mg of intratumoral prodrug.
Figure 5B:
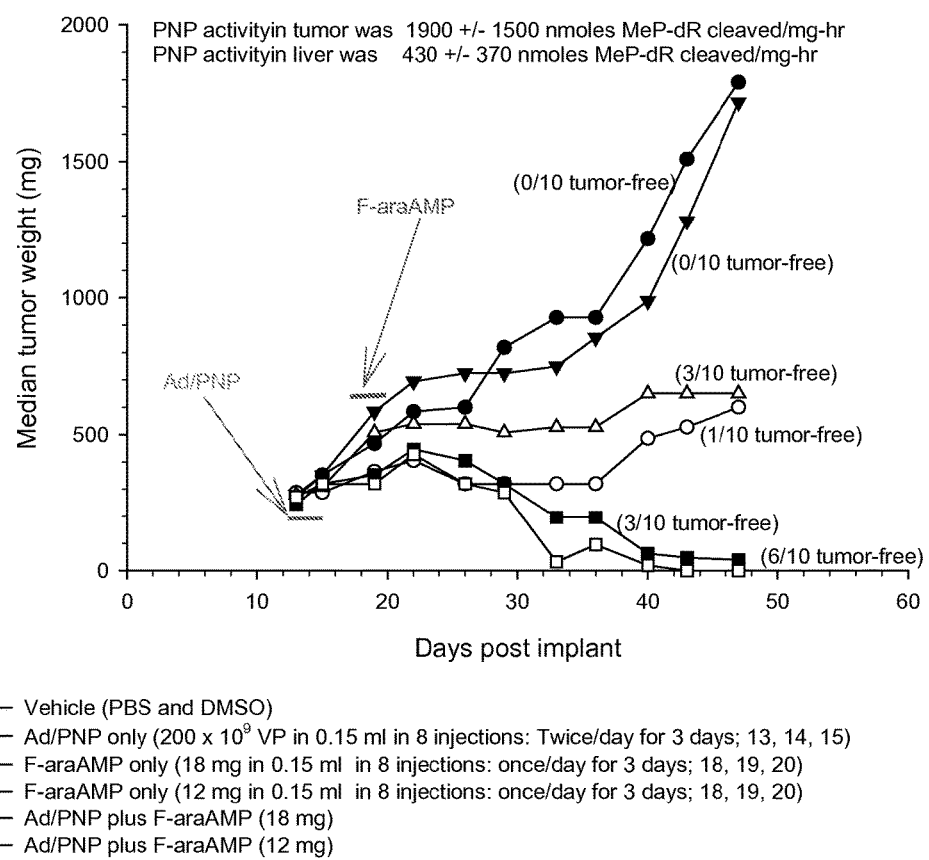
FIG. 5B is a plot of tumor weight as a function of time showing the effect of adenoviral vector (Ad) PNP plus F-araAMP on D54 tumors at a lower F-araAMP dosing regime (18 mg)

Modest antitumor activity after intratumoral (IT) injection of a replication deficient adenoviral vector expressing *E. coli* PNP (Ad/PNP) followed by systemic treatment with F-araAMP has been demonstrated (Hong et al. *Cancer Res.* 2004; 64: 6610-6615). Based on the robust activity demonstrated in FIG. 2C when high doses of F-araAMP are administered IT, the antitumor activity of Ad/PNP plus F-araAMP when both of these components are inoculated directly into a tumor mass is investigated (FIG. 5A). In the experiment shown, $2 \times 10^{11}$ VP of Ad/PNP are administered IT twice per day for 3 days (days 15, 16, and 17) for a total of 6 injections. The tumors are subsequently inoculated with 24 mg of F-araAMP once per day on Days 20, 21, and 22. *E. coli* PNP activity in the tumors on day 20 (the first day of F-araAMP treatment) is 7,500±2,000 units, which is similar to that observed for tumors in which 5 to 10% of the cells stably expressed the enzyme (2,500, 14,300, or 8,600 units) and within the range for which robust antitumor activity attributable to IT F-araAMP is expected. Although 2 of 10 mice treated with Ad/PNP plus F-araAMP died, there is an excellent antitumor effect in the 8 surviving mice that experienced 17% weight loss during treatment that later resolved. Because of the evidence of toxicity noted in the experiment shown in FIG. 5A, the study is repeated at a reduced dose of F-araAMP (18 mg/injection). With this schedule, there are no drug related deaths in the treatment group, and although murine body weights did not decrease, prolonged antitumor activity is noted through day 71 post implant (FIG. 5B). The *E. coli* PNP activity in the tumors of this experiment is 1,900±1,500 units. The results establish that intratumoral injection of Ad/PNP followed by IT F-araAMP can elicit a substantial regressive effect on otherwise refractory solid tumors that is superior to that seen after intratumoral injection of Ad/PNP followed by IP F-araAMP (Hong et al. *Cancer Res.* 2004; 64: 6610-6615).

Injection of tumors with both Ad/PNP plus higher doses of F-araAMP had a dramatic effect on tumor growth (FIGS. 5A and 5B), which is superior to Ad/PNP plus systemic F-araAMP.

Example 8. Effect of F-dAdo Versus F-araAMP

Figure 5C:
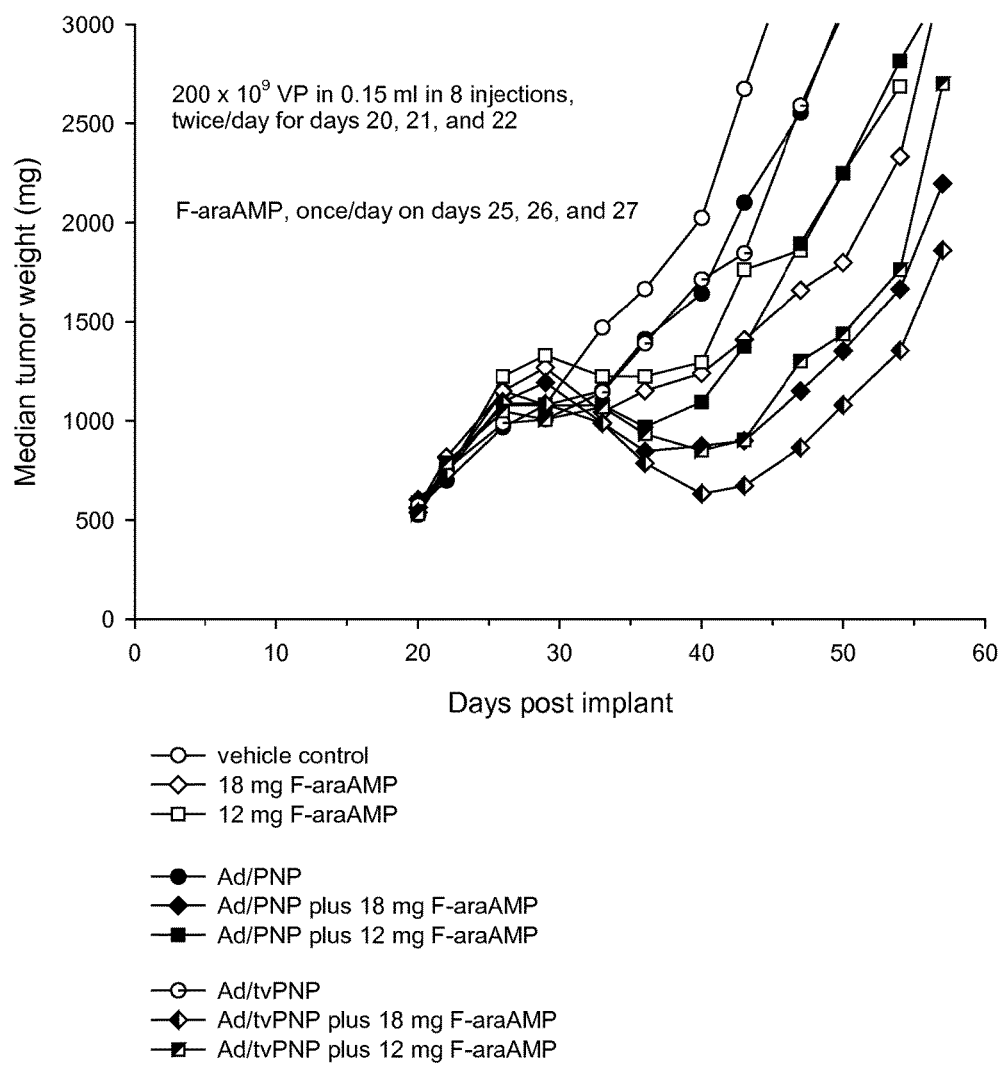
FIG. 5C is a plot of tumor weight as a function of time showing the effect under varied sequences of direct intratumoral administration and differing origin PNP sequences.

F-dAdo or F-araAMP is injected 3 times into D54 tumors in 150 µl volumes in 8 separate injections of approximately 20 µl each. In FIG. 5A, parental D54 human glioma tumors are treated IT with vehicle (closed circles), Ad/PNP (open circles), F-araAMP (filled triangles), or Ad/PNP plus F-araAMP (open triangles). Ad/PNP ($2 \times 10^{11}$ VP) is injected twice a day for 3 consecutive days starting on day 15. Twenty four mg F-araAMP dissolved in DMSO is injected into tumors once per day for 3 consecutive days starting on day 20. The tumors in vehicle treated mice are injected 6 times with saline followed by 3 injections of DMSO (otherwise as described above). The activity of *E. coli* PNP in the D54 tumors (on day 20) is 7,500±2,000 PNP units. Each treatment arm contains 10 mice. In the combined treatment arm, two of ten mice are lost prior to completion. Four of the eight remaining mice are tumor-free on day 65, two mice have small tumors (63 and 288 mg), and two mice had growing tumors (1666 and 1584 mg). The tumor growth in mice treated with Ad/PNP plus F-araAMP is significantly different than that in mice treated with F-araAMP or Ad/PNP only (P=0.010 and 0.002, respectively). In FIG. 5B, mice are treated as described in FIG. 5A except that the dose of F-araAMP is 18 mg per injection. The activity of *E. coli* PNP on day 18 in this experiment is 1900±1500 PNP units. The tumor growth in mice treated with Ad/PNP plus F-araAMP is significantly different than that in mice treated with F-araAMP or Ad/PNP only (P=0.001 and 0.011, respectively). Data using an alternative source of *T. vaganalis* (Tv)-PNP is shown in FIG. 5C.

Figure 6A:
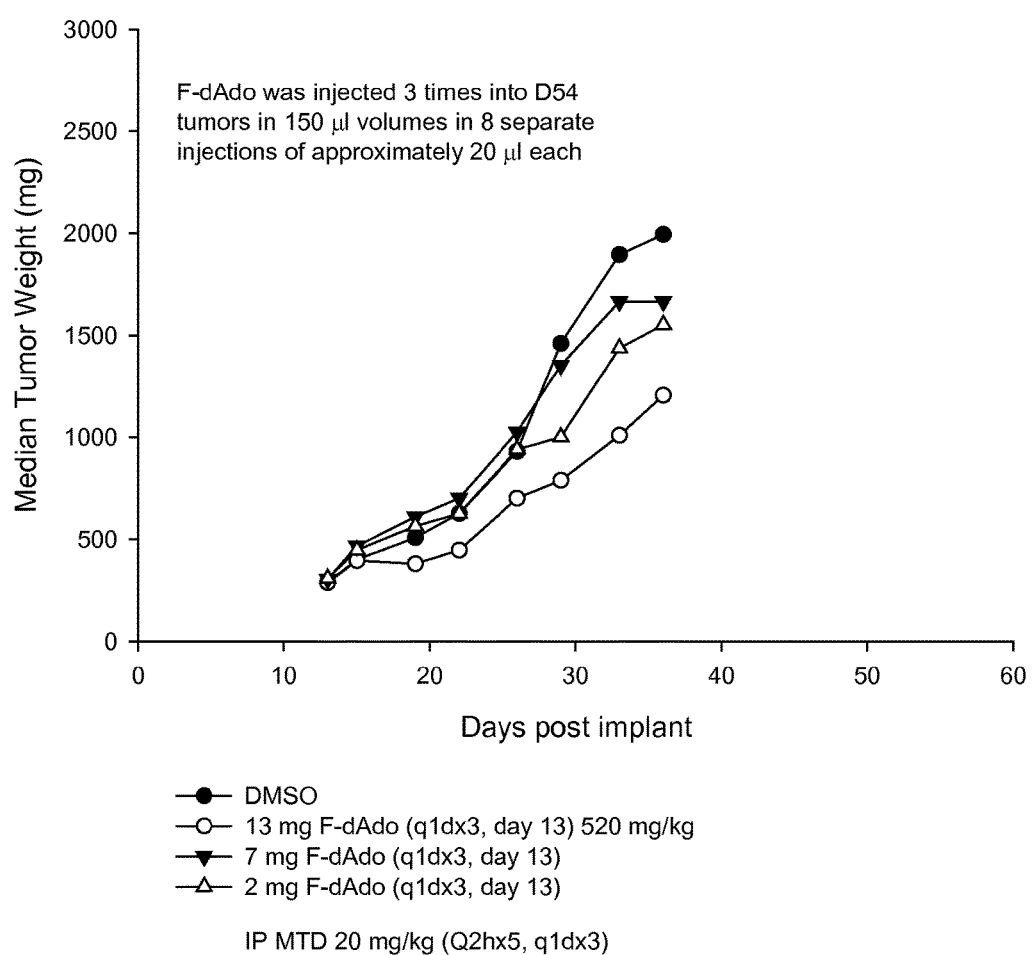
FIG. 6A is a plot of tumor weight as a function of time showing the efficacy of F-dAdo through direct intratumoral injection into tumors on D54 tumor growth, where none of the cells express *E. coli* PNP activity.
Figure 6B:
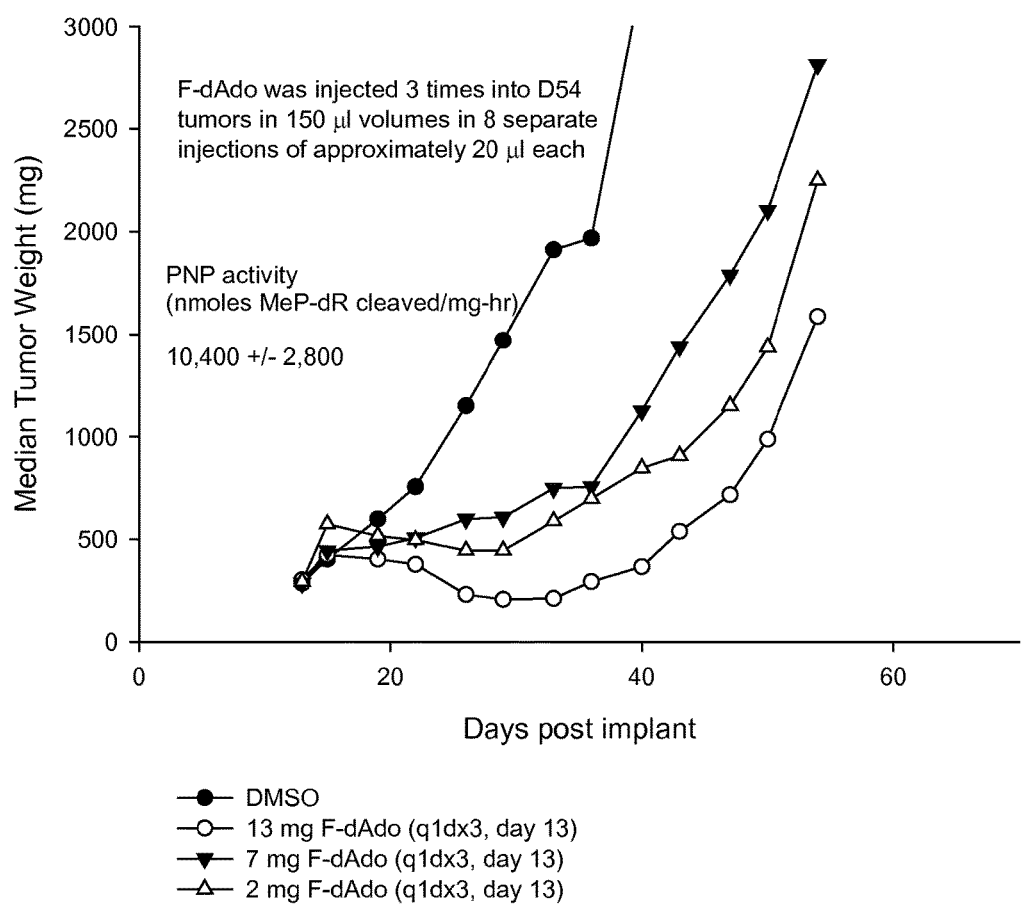
FIG. 6B is a plot of tumor weight as a function of time showing the efficacy of F-dAdo through direct intratumoral injection into tumors on D54 tumor growth in which 10% of the cells express *E. coli* PNP activity.

Better results are observed with F-araAMP than with F-dAdo (FIGS. 6A and 6B) although F-dAdo is a much better substrate for *E. coli* PNP than is F-araA when the cells express PNP.

Figure 7A:
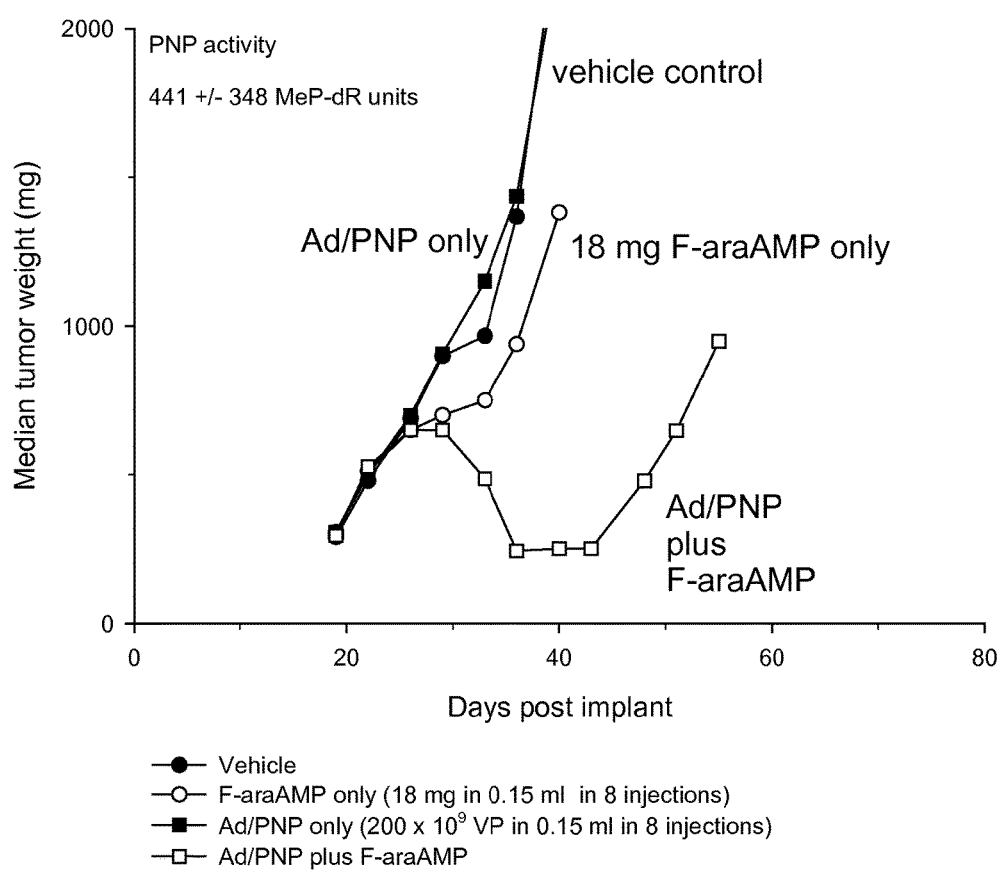
FIG. 7A is a plot of tumor weight as a function of time showing the effect of intratumoral F-araAMP and Ad/PNP on DU145 tumors.
Figure 7B:
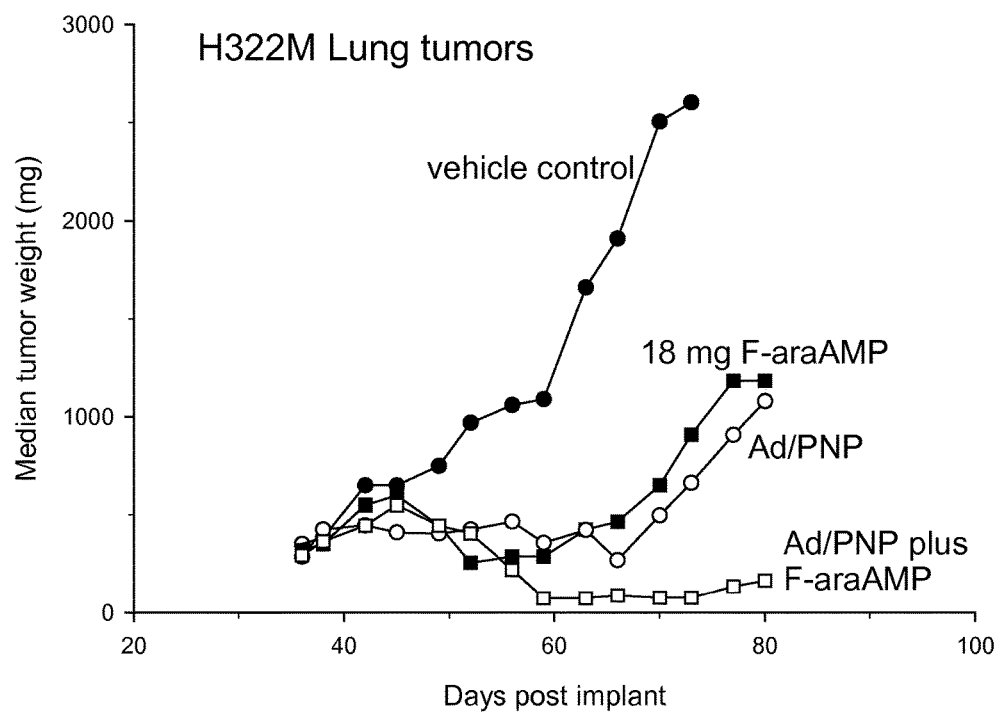
FIG. 7B is a plot of tumor weight as a function of time showing the effect of intratumoral F-araAMP and Ad/PNP NCI-H322M non-small cell lung adenocarcinoma tumors.

Example 9. Effect of Intratumoral F-araAMP and Ad/PNP on DU145 (Human Prostate) Tumors and NCI-H322M (Human Non-Small Cell Adenocarcinoma Lung) Tumors Injections of F-araAMP and Ad/PNP are performed as detailed above, with the exception that the tumors are now DU145 with similar results. (FIG. 7A). Injections of F-araAMP and Ad/PNP are performed as detailed above, with the exception that the tumors are now H322M with similar results. (FIG. 7B).

Figure 8A:
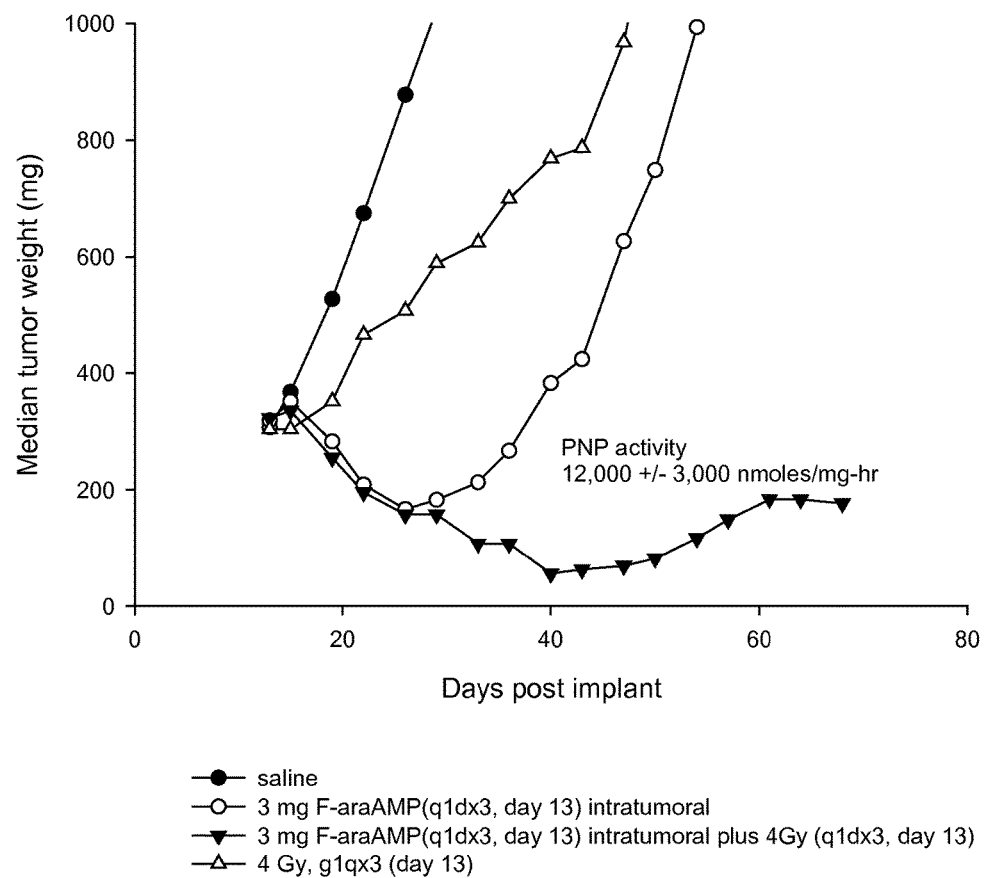
FIG. 8A is a plot of tumor weight as a function of time showing the effect of intratumoral injection of F-araAMP plus radiation on D54 tumors in which 10% of cells express *E. coli* PNP.
Figure 8B:
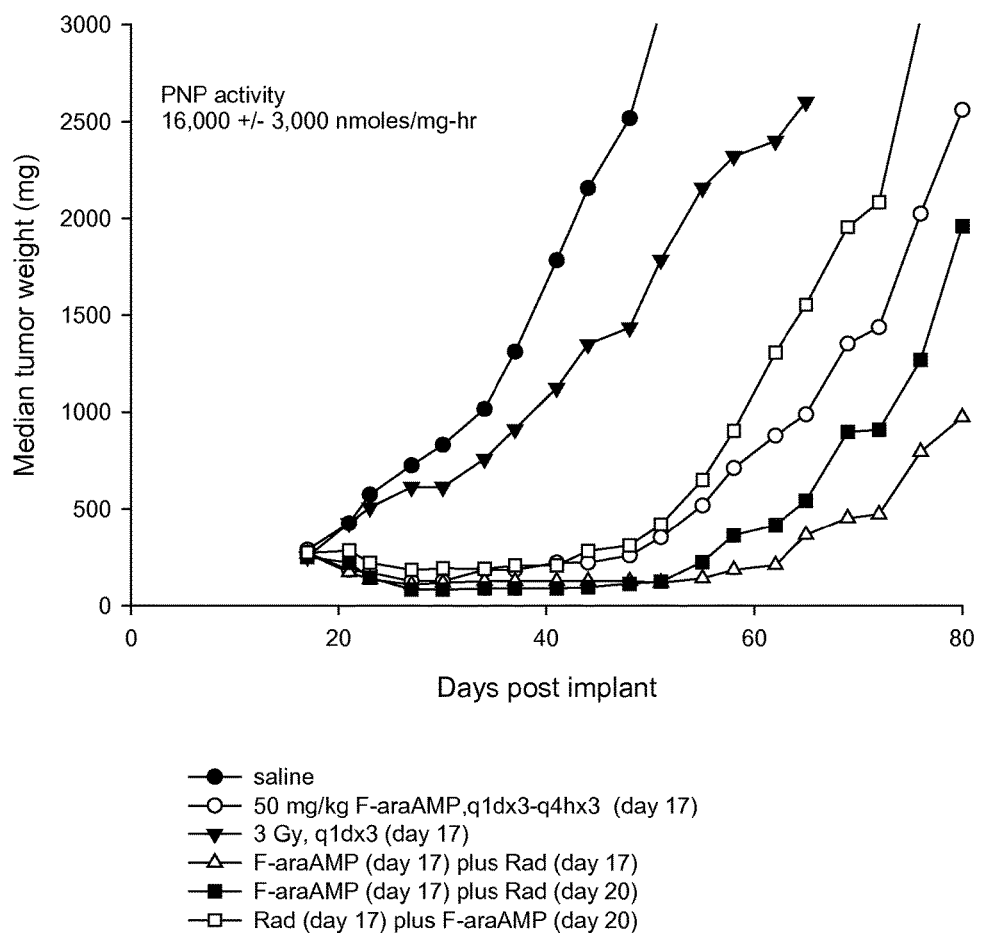
FIG. 8B is a plot of tumor weight as a function of time showing the effect of intraperitoneal (IP) injection of F-araAMP plus radiation on 10% D54/PNP tumors for varied radiation regimes.

Example 10. Effect of Intratumoral Injection of F-araAMP Plus Radiation on D54 Tumors Locally advanced solid tumors often become resistant to radiation therapy. As a test of adjuvant *E. coli* PNP in this setting, F-araAMP injection together with external beam radiation is investigated. In FIG. 8A, tumors in which 10% of cells express *E. coli* PNP are administered radiation (determined previously to confer a measurable effect on D54 tumor growth) with or without three IT injections of 3 mg of F-araAMP (a dose that resulted in tumor suppression but no tumor free-survivors, FIG. 2A). In FIG. 8B, tumors in which 10% of cells express *E. coli* PNP are administered radiation (determined previously to confer a measurable effect on D54 tumor growth) with or without three systemic IP injections of 3 mg of F-araAMP (a dose that resulted in tumor suppression but no tumor free-survivors, FIG. 2A). Combining *E. coli* PNP/F-araAMP with radiation therapy resulted in a pronounced antitumor activity, which is much greater than either treatment alone. Ten to fourteen percent weight loss is observed in all treatment groups (which rapidly resolved after termination of treatment), indicating that toxicities of the two interventions are not additive. Similar results are obtained with the sustained release F-araAMP of Example 5.

D54 tumor cells in which 10% of cells expressed *E. coli* PNP are injected sc into the flanks of nude mice. The tumors are treated with radiation, F-araAMP, or F-araAMP plus radiation. In two treatment groups, tumors are injected once per day for 3 consecutive days with 150 µl of either saline or 3 mg F-araAMP dissolved in saline. In two other treatment groups radiation (4 Gy) is administered once per day for 3 consecutive days 3 hours after injection of 150 µl of either saline (filled squares) or 3 mg F-araAMP dissolved in saline (open squares). The activity of *E. coli* PNP in the D54 tumors (on day 16) is 12,000±3,000 units. The tumor growth in mice treated with radiation plus F-araAMP is significantly different than that in mice treated with F-araAMP or radiation only (P=0.004 and <0.001, respectively) and superior for IT injection (FIG. 8A), as compared to systemic IP injection (FIG. 8B).

Example 11. Radioactivity in D54 Tumors After Intratumoral Injection of F-araAMP In an effort to understand the pharmacodynamics of intratumoral (IT) F-araAMP, the levels of prodrug activation in parental (D54) tumors and tumors in which 10% of cells expressed *E. coli* PNP are monitored (Table 1). Tumor tissue is collected 10 minutes or 4 hours after IT injection of 3 mg [$^3$H]-F-araAMP and the amount of radioactivity remaining in the tumor mass determined. Ten minutes after injection with F-araAMP, there are no differences between parental and D54 tumors in which 10% of cells express *E. coli* PNP. By 4 hours, radioactivity in D54 tumors that expressed *E. coli* PNP is substantially higher than parental tumors, representing the amount of F-araAMP converted to F-Ade metabolites. The experiment indicated that 190 nmoles of F-Ade metabolites are generated and retained per gram of tumor tissue after intratumoral injection of 3 mg F-araAMP. Three mg of F-araAMP is equal to 8200 nmoles, and since tumors in this experiment are approximately 0.3 grams, approximately 57 nmoles of F-Ade are retained in the tumor tissue in this experiment, or 0.7% of the total F-araAMP injected into the tumor.

TABLE 1

Radioactivity in D54 tumors after intratumoral injection of F-araAMP

| | nmoles F-araAMP/gram of tissue | |
|---|---|---|
| | 10 min | 4 hours |
| D54 tumors | 980 ± 730 | 31 ± 6 |
| 10% PNP D54 tumors | 1100 ± 990 | 220 ± 75* |

Three mg (8,200 nmoles) of [$^3$H]F-araAMP (10 µCi/injection) are injected into D54 tumors or D54 tumors in which 10% of the cells express *E. coli* PNP as described in FIG. 2. Tumors (approximately 300 mg) are removed 10 minutes and 4 hours after injection with F-araAMP and the amount of radioactivity in each tumor determined. There are 4 tumors per group. This experiment has been repeated with similar results. *Significantly different from D54 tumors: p<0.02, paired Student's t-test.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. The process of killing targeted cells present in a solid malignancy in a mammalian host subject comprising:
   delivering a purine nucleoside phosphorylase, the purine nucleoside phosphorylase having a sequence foreign to the mammalian host to the targeted cells;
   administering a prodrug cleaved by said purine nucleoside phosphorylase to release a purine base of 2-fluoroadenine cytotoxic to the targeted cells, said prodrug administered in at least three consecutive doses; and
   then exposing the targeted cells to X-ray radiation at least three hours after a last of the at least three consecutive doses to kill the targeted cells in the solid malignancy in the mammalian host.

2. The process of claim 1 wherein said prodrug is administered by intratumoral injection into a non-cycling compartment of said solid malignancy.

3. The process of claim 1 wherein said purine nucleoside phosphorylase is delivered with a viral vector containing a nucleic acid encoding said purine nucleoside phosphorylase.

4. The process of killing targeted cells present in a solid malignancy in a mammalian host subject comprising:
   delivering a purine nucleoside phosphorylase, wherein said purine nucleoside phosphorylase is a tailed mutant, the purine nucleoside phosphorylase having a sequence foreign to the mammalian host to the targeted cells;
   administering a prodrug cleaved by said purine nucleoside phosphorylase or nucleoside hydrolase to release a purine base cytotoxic to the targeted cells; and
   then exposing the targeted cells to X-ray radiation to kill the targeted cells in the solid malignancy in the mammalian host.

5. The process of claim 1 further comprising a sustained release carrier of a gel, paste, or a microparticle for said prodrug.

6. The process of claim 1 wherein said purine nucleoside phosphorylase is intermixed with said prodrug prior to delivery.

7. The process of claim 3 wherein said viral vector is an adenoviral vector.

8. The process of claim 1 wherein said purine nucleoside phosphorylase is derived from *E. coli*.

9. The process of claim 1 wherein said prodrug is fludarabine phosphate.

10. The process of claim 1 further comprising exposing the targeted cells to X-ray radiation on at least three consecutive days.

11. The process of claim 1 wherein the at least three consecutive doses of the prodrug are administered on a daily basis.

12. The process of claim 1 further comprising inhibiting growth of bystander cells to the targeted cells.

13. The process of claim 12 wherein said bystander cells are cells within approximately 50 adjacent cell diameters or equivalent linear spacing of the targeted cells.

14. The process of claim 1 further comprising exposing the targeted cells to X-ray radiation on a daily basis until regression and prolonged inhibition of targeted cells results.

15. The process of claim 4 wherein the targeted cells are exposed to X-ray radiation for at least three consecutive days.

* * * * *